(12) United States Patent
Liu et al.

(10) Patent No.: US 7,609,875 B2
(45) Date of Patent: Oct. 27, 2009

(54) SCANNER SYSTEM AND METHOD FOR MAPPING SURFACE OF THREE-DIMENSIONAL OBJECT

(75) Inventors: Yongqian Liu, Richardson, TX (US); Phillip Getto, Plano, TX (US)

(73) Assignee: Orametrix, Inc., Richardson, TX (US)

( * ) Notice: Subject to any disclaimer, the term of this patent is extended or adjusted under 35 U.S.C. 154(b) by 914 days.

(21) Appl. No.: 11/139,454

(22) Filed: May 27, 2005

(65) Prior Publication Data
US 2006/0269896 A1 Nov. 30, 2006

(51) Int. Cl.
*G06K 9/00* (2006.01)
*A61C 3/00* (2006.01)
*G02F 1/11* (2006.01)

(52) U.S. Cl. .......................... 382/154; 433/24; 359/287
(58) Field of Classification Search .................. 382/154
See application file for complete search history.

(56) References Cited

U.S. PATENT DOCUMENTS

| | | | | |
|---|---|---|---|---|
| 6,040,929 A * | 3/2000 | Hasegawa et al. | ............. | 359/17 |
| 6,059,188 A * | 5/2000 | diFazio et al. | .......... | 235/462.36 |
| 6,386,878 B1 * | 5/2002 | Pavlovskaia et al. | ........ | 433/215 |
| 6,493,097 B1 * | 12/2002 | Ivarsson | ..................... | 356/630 |
| 6,625,341 B1 * | 9/2003 | Novotny | ..................... | 385/18 |
| 6,648,640 B2 * | 11/2003 | Rubbert et al. | ................ | 433/24 |
| 6,785,433 B2 * | 8/2004 | Tiefenthaler | ................. | 385/12 |
| 2002/0141026 A1 * | 10/2002 | Wiklof et al. | ............... | 359/212 |
| 2002/0179828 A1 * | 12/2002 | Engelhardt et al. | .......... | 250/234 |
| 2003/0063367 A1 * | 4/2003 | Widzgowski | ............... | 359/287 |
| 2003/0085849 A1 * | 5/2003 | Grabert | ....................... | 345/30 |
| 2003/0100824 A1 * | 5/2003 | Warren et al. | ............... | 600/407 |
| 2003/0155667 A1 * | 8/2003 | Devoe et al. | ................ | 264/1.27 |
| 2003/0178584 A1 * | 9/2003 | Arnone et al. | ........... | 250/495.1 |
| 2004/0155665 A1 * | 8/2004 | Arnone et al. | ............. | 324/644 |
| 2005/0058352 A1 * | 3/2005 | Deliwala | .................... | 382/232 |

* cited by examiner

*Primary Examiner*—Bhavesh M Mehta
*Assistant Examiner*—David P Rashid
(74) *Attorney, Agent, or Firm*—Jasvantrai C. Shah

(57) ABSTRACT

A scanning system is disclosed including a hand-held scanning device for capturing three-dimensional information of an object. The scanner system includes a high-speed transceiver having a high-speed laser light source, a high frequency MEMS oscillating scanning mirror and software for frame registration. Laser based range finding technique is used to map the scanned object. MEMS oscillating at high speed enables rapid and accurate scanning of an object. The scanning can be performed without knowledge or even precise control of the position of the object relative to the scanner. Random movement of the object during scanning is also possible. The scanner can be used for a variety of purposes, including medical and industrial purposes. The illustrated embodiment is in-vivo scanning of human teeth for purposes of orthodontic treatment planning and diagnosis. Several benefits from the scanner are possible: much higher resolution of the scanned object, improved acquisition speed of the three-dimensional information of the surface of the object to be mapped, and the improvement in virtual image clarity.

56 Claims, 8 Drawing Sheets

SCANNER SYSTEM AND METHOD FOR MAPPING SURFACE OF THREE-DIMENSIONAL OBJECT

BACKGROUND OF THE INVENTION

A. Field of the Invention

This invention relates generally to a system for scanning a three-dimensional object. The scanning system utilizes a laser-based range finding technology coupled with a scanning mirror, such as a Micro-Electro-Mechanical Systems (MEMS) mirror, oscillating at a high frequency, and a high-speed transceiver. The scanning system acquires surface information of the scanned object and generates an accurate three-dimensional computer model of the object from the captured information.

The inventive scanning system and method can be used to analyze the surface and three-dimensional shape of virtually any three-dimensional object, including work pieces and manufactured objects, art objects, archaeological artifacts, and large scale structures such as rooms and buildings. The invention is particularly useful in medical-related applications, including orthodontics, and the present document discusses the invention in the context of orthodontics and the scanning of teeth (either scanning in-vivo or a scanning a physical model). However, other uses of the scanner and method are of course within the scope of the invention.

B. Description of Related Art

Scanners are devices for capturing and recording information from a surface of an object. Scanners for obtaining information from a two-dimensional surface, such as reading bar codes or characters printed on a piece of paper, are widely known. Several scanners have been proposed for recording three-dimensional information as well.

Dentistry and orthodontics is one area where precise knowledge of a patient's dentition is desirable, and hence this is one area where three-dimensional scanners have been proposed. The key to efficiency in treatment and maximum quality in results is a realistic simulation of the treatment process. Today's orthodontists have the possibility of taking plaster models of the upper and lower jaw, cutting the cast into single tooth models and sticking these tooth models into a wax bed, lining them up in the desired position, the so-called set-up. The next step is to bond a bracket at every tooth model. This would tell the orthodontist the geometry of the wire to run through the bracket slots to receive exactly this result. To make sure that the brackets will be bonded at exactly this position at the real patient's teeth, small templates for every tooth would have to be fabricated that fit over the bracket and a relevant part of the tooth and allow for reliable placement of the bracket at the patient. To increase efficiency of the bonding process, another option would be to transfer each single bracket onto a model of the malocclusion and then fabricate one single transfer tray per jaw that covers all brackets and relevant portions of every tooth. However, it is obvious that such an approach requires an extreme amount of time and labor.

U.S. Pat. Nos. 4,837,732 and 4,575,805 to Brandestini and Moermann propose a scanning system for in vivo, non-contact scanning of teeth. The patents describe a procedure for optically mapping a prepared tooth with a non-contact scan-head. The scan-head delivers the contour data, converted to electrical format, to be stored in a memory. A computer reads the memory following a line scan pattern. A milling device is slaved to follow this pattern by means of position control signals and mills an implant for the prepared tooth cavity.

The scan-head of the '732 and '805 patents includes a light emitting diode, with integral lens that radiates light onto the cavity. Before reaching the object, the rays of light are reflected by a mirror and pass through a ruling consisting of a plurality of parallel slits, or an alternating pattern of parallel opaque and transparent stripes. A lens focuses the reflected light onto a charge-coupled device (CCD) sensor. Depth information is determined in accordance with a principle known as "active triangulation." Basically, the object is viewed under an angle different from the incident rays due to a parallax effect. Each light stripe will have an apparent positional shift and the amount of the shift at each point along each light stripe is proportional to the vertical height of the corresponding portion of the surface on the object.

U.S. Pat. No. 5,372,502 to Massen et al. describes an optical probe for measuring teeth that works on a similar principle. As noted in the Massen et al. patent, the Brandestini et al. technique is difficult to use when there are large variations in surface topography since such large jumps displace the pattern by an amount larger than the phase constant of the pattern, making it difficult to reconstruct the pattern of lines. Furthermore, precise knowledge of the angle of incidence and angle of reflection, and the separation distance between the light source and the detector, are needed to make accurate determinations of depth. Furthermore, the scanner has to be rather carefully positioned with respect to the tooth and would be unable to make a complete model of the dentition.

U.S. Pat. No. 5,027,281 to Rekow et al. describes a scanning method using a three axis positioning head with a laser source and detector, a rotational stage and a computer controller. The computer controller positions both the rotational stage and the positioning head. An object is placed on the rotational stage and the laser beam reflects from it. The reflected laser beam is used to measure the distance between the object and the laser source. X and Y coordinates are obtained by movement of the rotational stage or the positioning head. A three-dimensional virtual model of the object is created from the laser scanning. The '281 patent describes using this scanning method for scanning a plaster model of teeth for purposes of acquiring shape of the teeth to form a dental prosthesis. The system of the '281 patent is not particularly flexible, since it requires the object to be placed on the rotational stage and precise control of the relative position of the object and the positioning head is required at all times. It is unsuited for in vivo scanning of the teeth.

U.S. Pat. No. 5,431,562 to Andreiko et al. describes a method of acquiring certain shape information of teeth from a plaster model of the teeth. The plaster model is placed on a table and a picture is taken of the teeth using a video camera positioned a known distance away from the model, looking directly down on the model. The image is displayed on an input computer and a positioning grid is placed over the image of the teeth. The operator manually inputs X and Y coordinate information of selected points on the teeth, such as the mesial and distal contact points of the teeth. An alternative embodiment is described in which a laser directs a laser beam onto a model of the teeth and the reflected beam is detected by a sensor. The patent asserts that three-dimensional information as to teeth can be acquired from this technique but does not explain how it would be done. Neither of the techniques of Andreiko has met with widespread commercial success or acceptance in orthodontics. Neither technique achieves in vivo scanning of teeth. Moreover, the video technique does not produce complete three-dimensional information as to the teeth, but rather a limited amount of two-dimensional information, requiring significant manual operator input. Even using this technique, additional equipment is required even to describe the labial surface of a tooth along a single plane.

U.S. Pat. No. 5,309,212 to Clark describes an optical scanning rangefinder that creates a depth map of its surroundings by scanning a beam of modulated, collimated light and observing reflections from proximate surfaces. The scanning system uses dual rotating prisms to deflect the transmitted beam and collect a portion of the reflected light, which is focused on a photo detector and converted to an electrical signal. This signal is amplified, AC coupled, and inverted. The inverted signal drives the modulator for the light source. When sufficient light is received by the detector, this system forms an oscillator, the frequency of which depends on the distance to the illuminated surface. This frequency is measured, and the distance to the surface derived from it.

U.S. Pat. No. 6,088,085 to Wetteborn discloses a range measurement apparatus, in particular a single beam pulsed laser range finder, comprising a light transmitter, a light receiver, an optical attenuator disposed in the transmission or reception branch and a time measuring unit for determining the light transit time between the transmission and the receipt of a light signal. The light transmitter is formed as a unitary and compact module into which a laser diode, connection elements for the laser diodes, an apparatus for coupling out the reference pulse, and also a fiber plug connector for the coupling of the transmitted light into a light conducting fiber are integrated. The light receiver is likewise formed as a unitary and compact module into which a photodiode, connection elements for the photodiode, an apparatus for coupling in the reference pulse and also a fiber plug connector for the coupling in of the received light which takes place via a light conducting fiber are integrated.

U.S. Pat. No. 6,246,468 to Dimsdale and U.S. Pat. No. 6,330,523 to Kacyra, et al. each discloses an integrated system for generating a model of a three-dimensional object. A scanning laser device scans the three-dimensional object and generates a point cloud. The points of the point cloud each indicate a location of a corresponding point on a surface of the object. A first model is generated, responsive to the point cloud, that generates a first model representing constituent geometric shapes of the object. A data file is generated, responsive to the first model, that can be inputted to a computer-aided design system.

U.S. Pat. No. 6,437,853 to Seo discloses a three-dimensional image capturing device which performs a distance measurement in first and second modes. In the first distance measurement mode, an electric charge accumulation period starts at the fall of a pulse of a distance measuring light beam, and ends after the fall of a pulse of a reflected light beam. In the second distance measurement mode, an electric charge accumulation period starts earlier than the fall of a pulse of the distance measuring light beam, by a predetermined time, and ends after the fall of a pulse of the reflected light beam. Based on a ratio of a first accumulated electric charge amount, obtained by the first distance measurement mode, to a second accumulated electric charge amount, obtained by the second distance measurement mode, the three-dimensional image is obtained.

U.S. Pat. No. 6,648,640 to Rubbert, et al. describes an interactive, computer based orthodontist treatment planning, appliance design and appliance manufacturing method and system. A scanner is described which acquires images of the dentition that are converted to three-dimensional frames of data. The data from the several frames are registered to each other to provide a complete three-dimensional virtual model of the dentition. Individual tooth objects are obtained from the virtual model. A computer-interactive software program provides for treatment planning, diagnosis and appliance design from the virtual tooth models.

U.S. Pat. No. 6,661,500 to Kindt, et al. discloses an image sensor that contains pixel cells that can individually provide a real-time output signal that is proportional to the instantaneous magnitude of incident radiation upon each pixel cell. The individual real-time output signals can be used to construct an electronic image. Additionally, the pixel cells of the image sensor can be used to collectively provide an accumulated real-time output signal that is proportional to the instantaneous magnitude of incident radiation upon a plurality of selected pixel cells. A propagated signal from a source such as a laser can be used to illuminate a target in an image. A reflection from the target can be detected in the accumulated real-time output signal. The range to the target can be determined using the round-trip propagation time between the sensor and the target of a propagated signal.

U.S. Pat. No. 6,674,895 to Rafii, et al. discloses a three-dimension distance time-of-flight system in which distance values are acquired by a plurality of sensors independently from each other. For use with this and similar systems, Z-distance accuracy and resolution are enhanced using various techniques including over-sampling acquired sensor data and forming running averages, or forming moving averages. Acquired data may be rejected if it fails to meet criteria associated with distance, luminosity, velocity, or estimated shape information reported by neighboring sensors. A sub-target having at least one pre-calibrated reflectance zone is used to improve system measurement accuracy. Elliptical error is corrected for using a disclosed method, and reversible mapping of Z-values into RGB is provided.

U.S. Pat. No. 6,697,164 to Babayoff, et al. discloses a method of determining surface topology of a portion of a three-dimensional structure. An array of incident light beams passing through a focusing optics and a probing face is shone on the portion. The beams generate illuminated spots on the structure and the intensity of the returning light rays propagating in an optical path opposite to that of the incident light rays is measured at various positions of the focal plane(s). By determining spot-specific positions yielding a maximum intensity of the returned light beams, data is generated which is representative of the topology.

Rocher, et al., "Low cost projection device with a 2-dimensioinal resonant micro scanning mirror", MOEMS Display and Imaging Systems II, edited by Hakan. Urey, David L. Dickensheets, Proceedings of SPIE Vol. 5348 (SPIE, Bellingham, Wash., 2004) presents a demonstrator of a low cost image projection device based on a resonant 2-dimensional micro scanning mirror used for the deflection of a modulated laser beam. The mirror is operated at a low ratio of horizontal and vertical oscillation frequency. In particular, a ratio with a small shift from an integer value is used to enable a scan of the whole projection screen with a Lissajous pattern. The control circuit performs an excitation of both mirror axes by driving them with fixed frequency according to the response curves of the actuator. Programmable counters are used to generate the driving frequencies and to determine the actual beam position during the scanning process. That enables a very simple and low cost control circuit. A micro scanning mirror, fabricated at Fraunhofer IPMS, was used in the demonstrator set up. It is operated at oscillation frequencies of 1.4 kHz (slow axis) and 9.4 kHz (fast axis). The control circuit was realized and successfully tested with a FPGA implementation. The image resolution provided by the control circuit is 256×256 pixels.

Kilpelä, in a 2004 thesis entitled "Pulsed time-of-flight laser range finder techniques for fast, high precision measurement applications" from Department of Electrical and Information Engineering, University of Oulu, P.O. Box 4500, FIN-90014, Oulu, Finland, describes the development of high bandwidth (~1 GHz) TOF (time-of-flight) laser range finder techniques for industrial measurement applications in the measurement range of zero to a few dozen meters to diffusely reflecting targets. The main goal of the thesis has been to improve single-shot precision to mm-level in order to shorten the measurement result acquisition time. A TOF laser range finder consists of a laser transmitter, one or two receivers and timing discriminators, and a time measuring unit. In order to improve single-shot precision the slew-rate of the measurement pulse should be increased, so the optical pulse of the laser transmitter should be narrower and more powerful and the bandwidth of the receiver should be higher without increasing the noise level too much.

What the art has lacked is a high-speed, reliable, accurate, low-cost, and easily used scanning system that can quickly and automatically acquire three-dimensional information of an object, without requiring substantial operator input, and in particular one that can be held in the hand and used for in vivo scanning or scanning a model. The present invention meets this need.

SUMMARY OF THE INVENTION

A scanner system is provided for capturing three-dimensional information of an object. The object can be virtually any object under scrutiny, however the present document will describe an application in which the object is the dentition of a patient suffering from a malocclusion.

The scanning system enables three-dimensional surface information to be obtained with a very high degree of precision. Moreover, the scanning system can be used without requiring precise movement of the scanner, or requiring the object under scrutiny to be fixed in space. The scanner is able to generate precise three-dimensional surface information by simply moving the scanner over the surface of the object, such as by hand, in any manner that is convenient for the user, even if the object moves in any random direction during scanning within reasonable limits. Thus, the scanner can be used to capture the surface of a patient's dentition in a few minutes, even if the patient moves his/her head or jaw while the scanning is occurring. Precise knowledge of the spatial relationship between the scanner and the object is not required.

The scanner obtains coordinates of points or pixels on the surface of the object being scanned, which are processed in a computer to calculate the surface configuration of the object in three dimensions of space automatically, quickly, with high precision, and with essentially no human involvement other than the act of scanning. The precision or accuracy will be dictated largely by the speed of the detection electronics and secondarily by the oscillation speed of the MEMS mirror. For teeth, an accuracy of under 20 microns is possible.

The surface configuration of the object in three dimensions of space can be represented as a mathematical model, i.e., a virtual model of the object, which can be displayed on any workstation or computer using available software tools. The mathematical model can be viewed in any orientation in space, permitting detailed analysis of the surface. The model can be compared to template objects stored in a computer. Deviations in the object from the template can be quantified and analyzed. Further, the virtual model can be transported from one computer to another computer anywhere in the world essentially instantaneously over communications links such as the Internet. The model can be replicated in a computer and thus be shared and used by multiple users simultaneously.

The scanner system is useful for a wide variety of industrial, medical, archeological, forensic, archival, or other purposes. Furthermore, the scanner can be scaled down in size such that it can be hand-held and used to scan small objects, e.g., teeth or small machined parts, or scaled up in size so that it can be used to make mathematical models of larger scale objects such as works of art, sculptures, archeological sites (e.g., the caves at Lascaux, France or the dwellings or kivas in Mesa Verde National Park), rooms or building facades.

In accordance with a preferred embodiment of the invention, the scanner system includes a high-speed transceiver having a high-speed laser light source, a MEMS scanning mirror oscillating at a high frequency, a high precision receiver or sensor and software for frame registration. Laser based range finding technique is used to map the scanned object. A novelty of this invention is that a MEMS mirror oscillating at a high speed enables rapid and accurate scanning of an object. In the preferred embodiment of the invention a two-dimensional MEMS, i.e. MEMS capable of rotation about two independent axes, is deployed. The basic scanning process is as follows: An optical beam emanates from the high-speed modulated or pulsed laser (preferably operating at 10 GHz or higher modulation speed) and is transmitted to the object being scanned using the following path: (a) first, the laser beam is collimated by a fiber collimator; (b) from the collimator the collimated laser beam is radiated towards a MEMS mirror; (c) the MEMS mirror in turn reflects the laser beam on to a beam splitter; (d) from there the light beam is focused through a lens and directed to a static mirror positioned at a desired angle; (e) the static mirror in turn directs the laser beam towards the surface of the object being scanned. The object reflects the laser beam that takes the following return path to a receiver: (a) first, the laser beam is reflected from the object back to the static mirror; (b) from there the beam is directed to the beam splitter through a lens; (c) and then to another lens and to a coupler; (d) from the coupler, the laser beam is reflected into a fiber which carries the laser beam to the receiver. In one embodiment of the invention, the round trip elapsed time from launching of the laser beam from the light source to reception of the beam reflected by the object at the receiver is measured to determine the Z coordinate, or the distance or depth of the point or pixel on the surface being scanned. Other techniques of determining the Z coordinate are described. During the scanning process, the MEMS mirror is oscillated at very high speeds along the x-axis and the y-axis; enabling rapid scanning. The high-speed receiver has a resolution better than 10 ps rise time. The modulation and detection method can use the standard direct modulation and phase shifting, frequency counting or chirped frequency modulation. Several benefits from the preferred embodiment of the scanner are possible. First, a much higher resolution is achieved due to the high speed optoelectronics integration, which improves resolution by a factor between two to three orders of magnitude. Second, the acquisition speed is improved. For small range applications such as oral scan, there are five orders of magnitude improvement in scan speed, where two orders of magnitude come from closer distance thus shorter round trip time to the object and three orders of magnitude come from mirror scanning speed improvement. Third, there is the improvement in signal-to-noise ratio and imaging clarity improvement compared to other 3D imaging technology.

In yet another embodiment of the invention for scanning a model the beam splitter and the static mirror are eliminated whereby the MEMS mirror directly reflects the laser beam on to the object being scanned.

In yet another embodiment of the invention, the reflection from the object being scanned is directly received by the beam splitter.

In yet another embodiment of the invention, a separate transmitter and a separate receiver are used in place of a transceiver.

In yet another embodiment of the invention, the static mirror is heated to prevent fogging in the in-vivo scanning application.

The scanning system can be constructed such that the memory, processing unit, and optical elements are in a single unit. Alternatively, the processing unit and memory can be located at a separate location, such as a scanning workstation or "scanning node", in order to reduce the size of the scanner per se. In such an embodiment, the scanner can be miniaturized into a hand-held device. A suitable cable or wireless communication medium connects the scanner device to the workstation to thereby supply the processing unit with scan data, and to receive commands (illumination commands, start/stop commands, etc.) from the workstation.

In an orthodontic embodiment of the scanner, it may be desirable to reduce the amount of equipment that is positioned proximate to the patient's chair. Hence, considerable latitude is possible in the configuration of the scanning system in terms of where processing, scanner illumination, or other functions are housed. Ideally, the scanner is connected via a cable or wireless communication medium to a base station for the scanner, the scanner workstation, and other equipment so as to provide the minimum amount of interference with the act of scanning at the chair side. The cable could for example be suspended from the ceiling.

In an orthodontic embodiment of the invention, the collimator, the MEMS device, the beam splitter, the lenses, the coupler and the additional static mirror are contained in a housing sized and shaped to be held in a human hand. The scanner is preferably capable of in-vivo scanning anatomical structures in the mouth. It is also suitable for scanning a plaster model of the teeth or even an impression of the teeth. All of these objects contain the same surface information, which is captured by the scanner. In a preferred embodiment, the processing of the images is performed in the scanning node, or other remote processing unit such as a back office orthodontic server. Alternatively, the computer processing of the images can be shared between two or more processing units, e.g., between the scanning workstation and the back office server, in order to reduce the amount of processing time. Furthermore, the scanning workstation may include a monitor operatively connected to the processing unit. The monitor displays three-dimensional images of the scanned object either during or after the processing unit has derived the spatial information of the object from the captured images.

In summary, a scanner system for capturing three-dimensional information of an object is disclosed. The scanning system comprises:

a light source emitting a laser beam towards an oscillating MEMS mirror;

the oscillating MEMS mirror reflecting the emitted laser beam towards the surface of an object being scanned; wherein the surface of the object reflects the emitted laser beam;

a receiver receiving the laser beam reflected by the surface of said object;

a processing unit recording the timing parameters of the emitted laser beam and the reflected laser beam and the oscillation angles of the oscillating MEMS mirror and computing there form a three-dimensional mapping information of the surface of the object; and a memory storing the computed three-dimensional mapping information of the object.

In another aspect of the invention, a method is provided for obtaining three-dimensional surface information of an object. The method includes the step of positioning a scanner proximate to the object. The term "proximate" here means that the distance between the scanner and the object is within the range of the optics of the scanner. The scanner has: (a) a light source emitting a laser beam; (b) an oscillating MEMS mirror reflecting the emitted laser beam towards the surface of an object being scanned; (c) a receiver receiving the reflection of the emitted laser beam from the surface of the object; (d) a processing unit computing three-dimensional mapping of the surface of the object from parameters of the emitted laser beam and the reflected laser beam; and (e) a memory storing the computed three-dimensional information of said object. The scanner and object are then moved relative to each other. For example, the object remains essentially stationary (or even moves slightly in some random manner) and the scanner is moved over the surface. The method continues with the step of capturing, with the scanning device, a series of frames off the object, while the scanner and the object move relative to each other. The method further includes the step of processing the series of frames of the object, each frame comprising spatial coordinates for a portion of the surface of the object in three dimensions. The frames are then registered to each other to thereby generate a virtual model of the object that is consistent with all the frames.

The processing step preferably comprises calculation of spatial coordinates in three dimensions for each of the specific pixels as follows: (a) calculating the z coordinate of the pixel using a range finding technique; and (b) calculating the x and y coordinates of the pixel.

These and various other aspects of the invention will be more readily appreciated from the following detailed description of a presently preferred embodiment of the invention. It will be understood that the scope of the invention is as set forth in the appended claims and that the invention is not considered limited to the various implementation details of the preferred and alternative embodiments described at length below.

BRIEF DESCRIPTION OF THE DRAWINGS

FIG. 8A illustrates an object 40 with example scanning frames 90. FIG. 8B illustrates the oscillation of the MEMS mirror along the x-axis while the MEMS mirror is kept in a fixed position along the y-axis; and the pattern of points or pixels that would be scanned on the surface of the object. Similarly, FIG. 8C illustrates the oscillation of the MEMS mirror along the y-axis while the MEMS mirror is kept in a fixed position along the x-axis; and the pattern of points or pixels that would be scanned on the surface of the object. FIG. 8D illustrates the pattern of points, and resulting frame, that would be realized when the MEMS mirror is simultaneously oscillated along the x-axis and along the y-axis.

FIG. 9A illustrates four oscillation cycles around the x-axis, FIG. 9B illustrates one oscillation cycle around the y-axis, and FIG. 9C illustrates super imposition of the x-axis oscillation cycles of FIG. 9A and the y-axis oscillation cycle of FIG. 9B.

FIG. 13A is an enlarged view of the scanned object.

DETAILED DESCRIPTION OF PREFERRED EMBODIMENT

Figure 1:
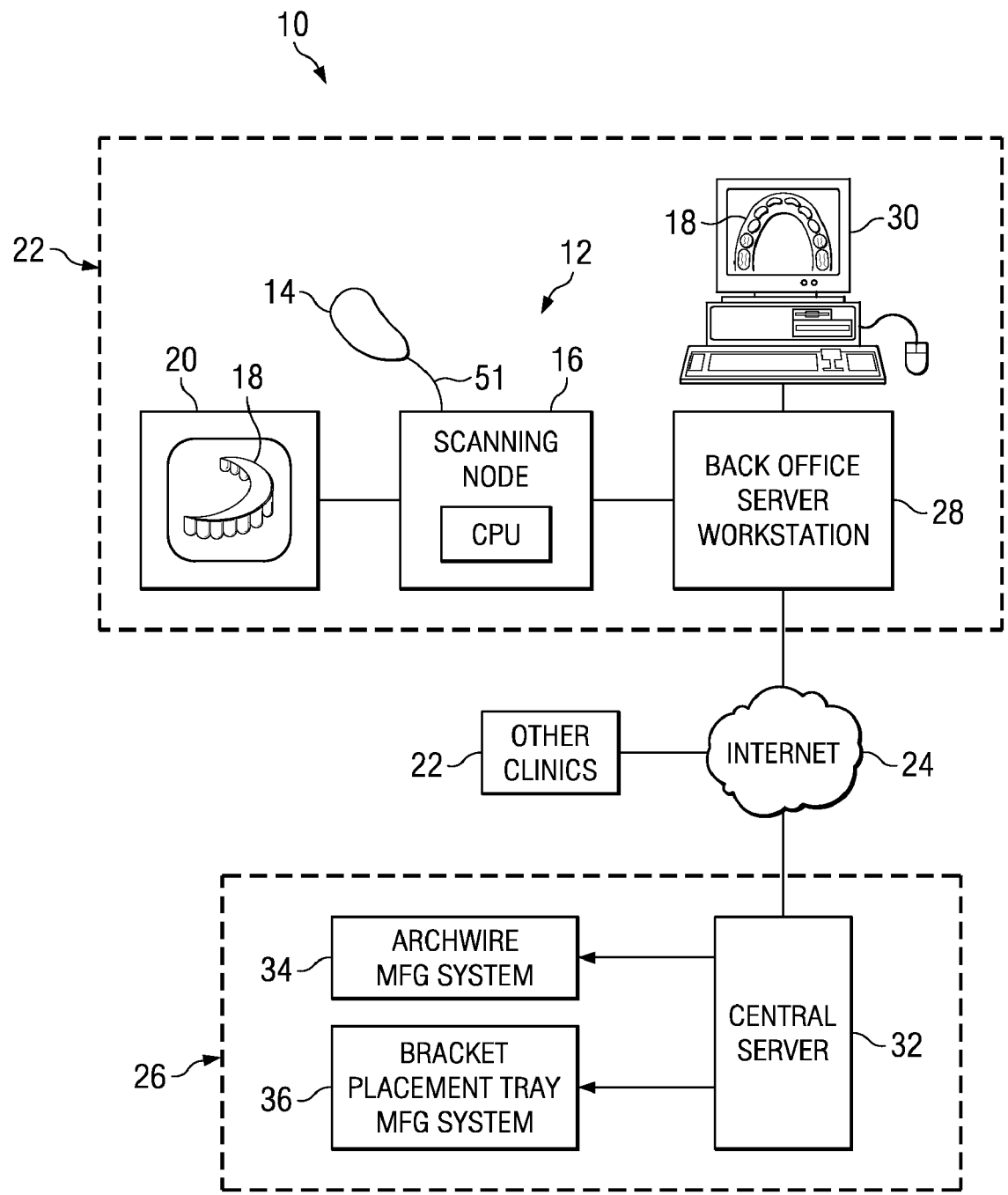
FIG. 1 is an illustration of an orthodontic care system incorporating a hand-held scanner system in accordance with a representative embodiment of the invention. The hand-held scanner is used by the orthodontist or the assistant to acquire three-dimensional information of the dentition and associated anatomical structures of a patient and provide a base of information to diagnose and plan treatment for the patient.

FIG. 1 is an illustration of an orthodontic care system 10 incorporating a scanner system 12 in accordance with a representative embodiment of the invention. The scanner system 12 includes a hand-held scanner 14 that is used by the orthodontist or his or her assistant to acquire three-dimensional information of the dentition and associated anatomical structures of a patient. The images are processed in a scanning node or workstation 16 having a central processing unit, such as a general-purpose computer. The scanning node 16, either alone or in combination with a back-office server 28, generates a three-dimensional computer model 18 of the dentition and provides the orthodontist with a base of information for diagnosis, planning treatment, and monitoring care for the patient. The model 18 is displayed to the user on a monitor 20 connected to the scanning node 16.

As noted above, the scanner system 12 described in detail herein is optimized for in-vivo scanning of teeth, or alternatively, scanning a plaster model of the teeth and/or an impression of the teeth. However, it will be apparent to persons skilled in the art that the scanning system 12 can by readily optimized for a variety of other diagnostic and/or treatment planning and/or monitoring uses in the medical arena. An example is scanning the face or head and planning plastic or orthopedic surgery. It can be readily adapted to virtually limitless number of applications in industrial, manufacturing, forensic, archeological, scientific, archival or other applications.

The orthodontic care system consists of a plurality of orthodontic clinics 22 which are linked via the Internet or other suitable communications medium 24 (such as the public switched telephone network, cable network, etc.) to a precision appliance service center 26. Each clinic 22 has a back office server workstation 28 having its own user interface, including a monitor 30. The back office server 28 executes an orthodontic treatment planning software program. The software obtains the three-dimensional digital data of the patient's teeth from the scanning node 16 and displays the model 18 for the orthodontist. The treatment planning software includes features to enable the orthodontist to manipulate the model 18 to plan treatment for the patient. For example, the orthodontist can select an archform for the teeth and manipulate individual tooth positions relative to the archform to arrive at a desired or target situation for the patient. The software moves the virtual teeth in accordance with the selections of the orthodontist. The software also allows the orthodontist to selectively place virtual brackets on the tooth models and design a customized archwire for the patient given the selected bracket positions. When the orthodontist has finished designing the orthodontic appliance for the patient, digital information regarding the patient, the malocclusion, and a desired treatment plan for the patient are sent over the communications medium to the appliance service center 26. A customized orthodontic archwire and a device for placement of the brackets on the teeth at the selected location is manufactured at the service center and shipped to the clinic 22. The invention is also applicable to other types of appliance systems besides brackets and archwires, such as removable aligning devices; retainers, Herbst appliances, etc.

As shown in FIG. 1, the precision appliance service center 26 includes a central server 32, an archwire manufacturing system 34 and a bracket placement manufacturing system 36. These details are not particularly important to the scanning system 12 per se and are therefore omitted from the present discussion for sake of brevity. For more details on these aspects of the illustrated orthodontic care system, the interested reader is directed to the patent application of Rüdger Rubbert et al., filed on Apr. 13, 2001, entitled INTERACTIVE AND ARCHWIRE-BASED ORTHODONTIC CARE SYSTEM BASED ON INTRA-ORAL SCANNING OF TEETH, Ser. No. 09/835,039, now issued as U.S. Pat. No. 6,648,640.

Figure 2:
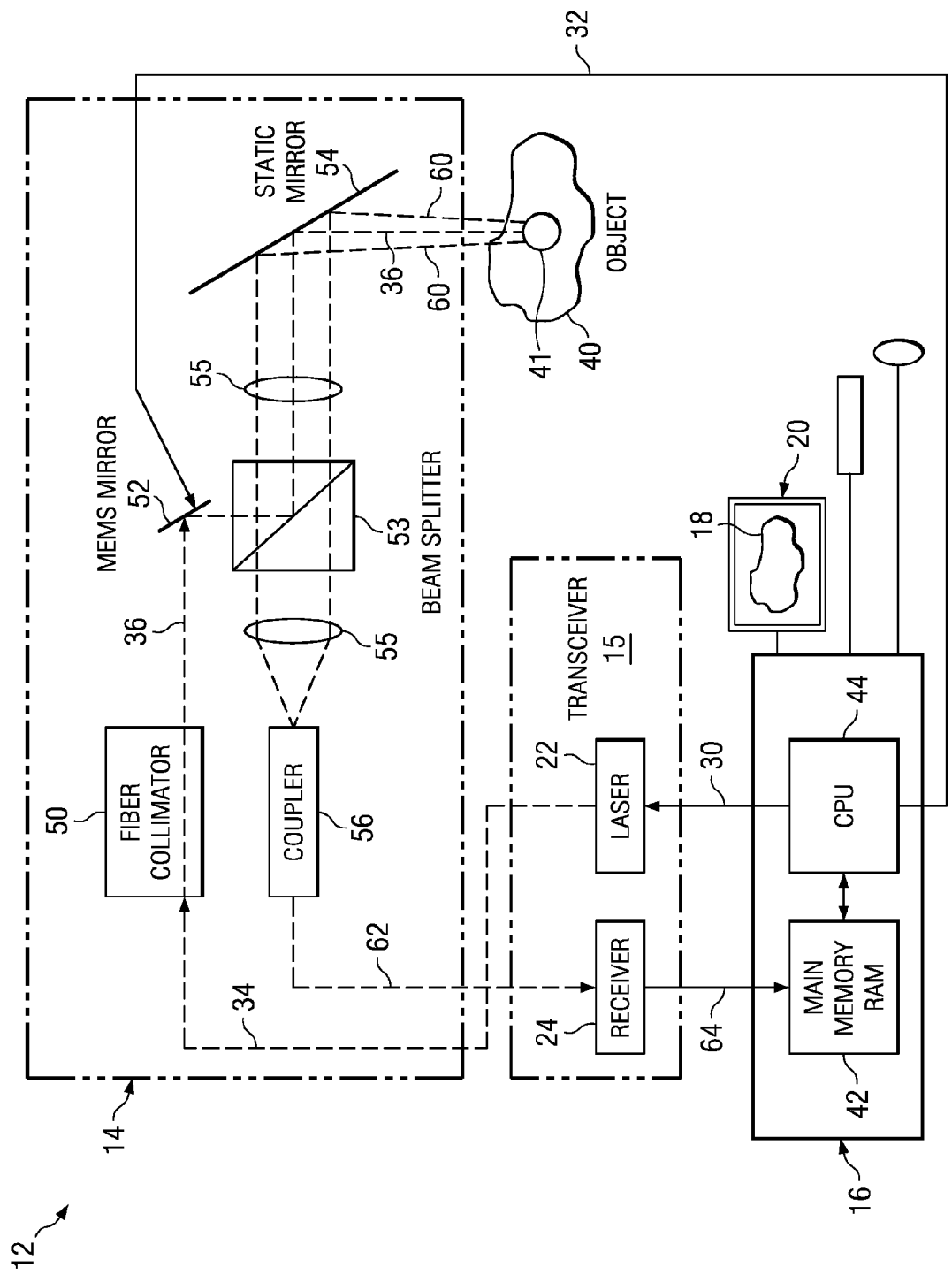
FIG. 2 is a block-diagram of a preferred embodiment of the scanning system, suitable for use in the orthodontic care system of FIG. 1.

FIG. 2 is a more detailed block-diagram of a preferred embodiment of the scanning system 12, suitable for use in the orthodontic care system of FIG. 1. The scanning system 12 is a mechanism for capturing three-dimensional information of an object 40. Although not displayed in FIG. 2, object 40 could very well be the dentition and surrounding anatomical structures of a human patient, e.g., gums, bone and/or soft tissue. The scanning system 12 utilizes a laser-based range finding technique for mapping the surface of a three-dimensional object. The scanning system 12 includes a scanner 14, a transceiver 15, and a processing system or workstation 16.

The basic function of the scanner 14 is to emit a laser beam towards the surface of the object being scanned and receive the reflection of the laser beam from a point on the surface of the object where the laser beam impacts the surface; thus enabling the identification or mapping of the point on the surface of the object through a range finding technique. In a preferred embodiment, the scanner 14 includes a fiber collimator 50, a MEMS mirror 52, a beam splitter 53, a mirror 54, two lenses 55, and a coupler 56. The collimator 50 receives a beam of light or a laser beam 34 from the laser source 22 and collimates the laser beam 34 into the laser beam 36 that is directed or emitted towards the object 40 through the MEMS mirror 52, the beam splitter 53, the lens 55 and the mirror 54. The laser beam 36 strikes the surface of the object at point 41 and is reflected back by the object as the light beam 60, which is received by the coupler 56 through the intervening mirror 54, the lenses 55 and the beam splitter 53. The reflected beam 60 is captured in the form of a cone of light as it leaves the object 40. The reflected beam comes out from the coupler 56 as the beam 62, which is received by the receiver 24. The time elapsed between the origination of the laser beam 34 from the laser source 22 and reception of the reflection 62 by the receiver 24 is measured in order to determine the range or distance of the point 41 on the object from the scanner. For ease of illustration, the point 41 is shown somewhat enlarged in FIG. 2. The MEMS mirror 52 is oscillated at a very high frequency, along the x-axis and the y-axis, so that a group of points or pixels are scanned from the surface of the object thus enabling high speed scanning of the object. The group of points scanned in this manner through oscillations of the MEMS mirror 52 while the user keeps the scanner 14 in a substantially stationary position forms a frame. Preferably the MEMS mirror 52 is oscillated by a control signal 32 from the workstation 16. The MEMS operation and acquisition of frames are described in greater detail later on in this document. The mirror 54 is stationary and provides a mechanism for guiding the light beams or the laser beams as shown in FIG. 2. One skilled in the art would appreciate that in another embodiment, the mirror 54 can be eliminated from the scanner 14.

The transceiver 15 includes a high-speed laser source 22 and a receiver 24. The laser 22 generates the light beam or the laser beam 34 which is carried to the fiber collimator 50 through a fiber (not shown in FIG. 2) and collimated into the light beam 36 by the fiber collimator 50. The laser 22 is controlled by a control signal 30 from the CPU 44. The control signal 30 turns the laser 22 on and off. The receiver 24 receives the returned light beam 62 from the coupler 56, which is a form of the reflected light beam 60.

The scanning workstation 16 provides control signal 30 to operate the laser 22 and control signal 32 to operate the MEMS mirror 52, as described earlier. The scanning workstation 16 receives data from the receiver 24 regarding the returned light beam 62 thus enabling the range finding calculations. The scanning workstation 16 also includes the monitor 20 for displaying the scanning results as a three-dimensional model 18 of the object 40 in real time as the scanning is occurring. The user interface also includes a keyboard and mouse for manipulating the virtual model of the object, and for entering or changing parameters for the scanning, identifying sections or segments of scans that have been obtained, and other features. The scanning station may also include a foot switch, not shown, for sending a signal to the CPU 44 indicating that scanning is commencing and scanning has been completed. The base station may alternatively include a voice recognition module that is trained to recognize a small set of voice commands such as START, STOP, AGAIN, REPEAT, SEGMENT, ONE, TWO, THREE, FOUR, etc., thereby eliminating the need for the foot switch. Scanner start and stop commands from the CPU 44, in the form of control signals, are sent to the laser source 22, thereby controlling the illumination of the laser 22 during scanning.

In summary, the novel high-speed scanning system 12 comprises three key elements: the high-speed transceiver 15, the high frequency MEMS scanning mirror 52 and the workstation 16 having software for frame registration. The optical beam emanates from the high-speed laser 22, which is then collimated by the fiber collimator 50, and is directed by a fast scanning MEMS mirror 52 through the beam splitter 53 and focusing lens 55 and the mirror 54 onto the object under imaging. The light beam reflected by the object is then received by the high-speed receiver 22 through the path that includes the mirror 54, the lenses 55, the beam splitter 53 and the coupler 56 as shown in FIG. 2. The laser signal modulation and detection methods utilize the standard direct modulation phase shifting and chirped frequency modulation. Several main improvements of the instant invention over the prior art are ensured with the technology implemented in the system. First is a much higher resolution due to the high-speed optoelectronics integration, which improves resolution by a factor between two to three orders of magnitude over the prior art. Second is the acquisition speed. For small range applications such as oral or in-vivo scan, there are five orders of magnitude improvement in scan speed over the prior art, where two orders of magnitude come from the closer distance thus shorter round trip time to the object and three orders of magnitude come from the mirror scanning speed improvement. Third is the improvement in signal-to-noise ratio and imaging clarity improvement compared to other 3D imaging technologies of the prior art.

Figure 3:
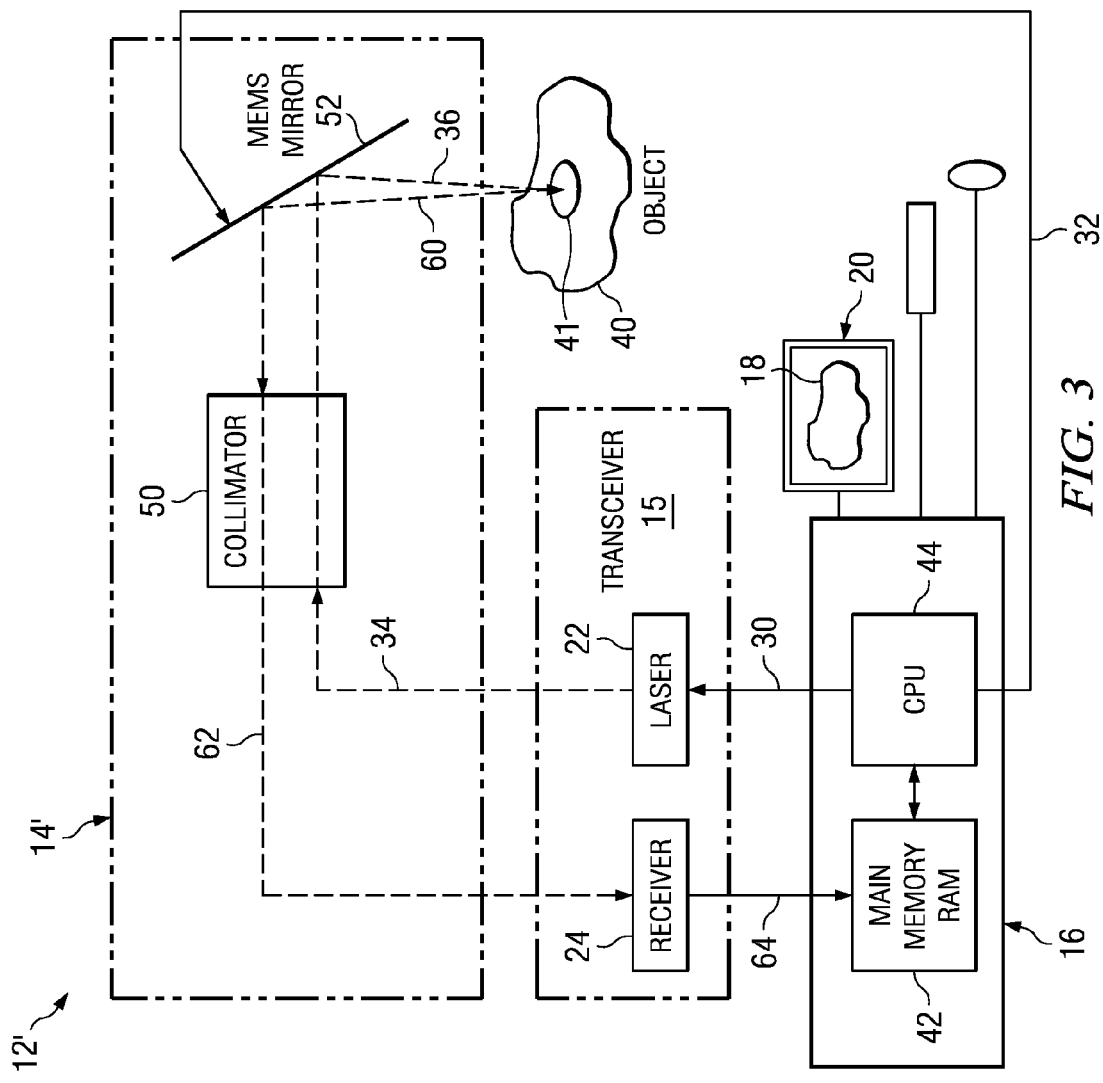
FIG. 3 is a block-diagram of another preferred embodiment of the scanning system, suitable for use in scanning the physical models in the orthodontic care system of FIG. 1.

FIG. 3 is a block-diagram of another preferred embodiment of the scanning system. The scanning system 12' also utilizes a laser based range finding technique for mapping the surface of an object in three-dimensions by means of scanning the object; and comprises a MEMS scanning mirror 52 which is oscillated at a high-speed, a high speed transceiver 15, and frame registration software in the workstation 16. The scanning system 12' includes a scanner 14', a transceiver 15 and a processing system or workstation 16.

In a preferred embodiment, the scanner 14' also includes a fiber collimator 50 and a MEMS mirror 52. The scanner 14' is used for directing a light beam 36 from the fiber collimator 50 using the MEMS mirror 52 on to the object 40 to be scanned, and for receiving the light beam 60 reflected from the object 40 via the MEMS mirror 52 into the fiber collimator 50. Preferably the MEMS mirror 52 is controlled by a control signal 32 from the workstation 16.

The transceiver 15 and the scanning workstation 16 of FIG. 3 provide essentially the same capabilities and functionalities as described for the transceiver 15 and the scanning workstation 16 of FIG. 2.

Figure 4:
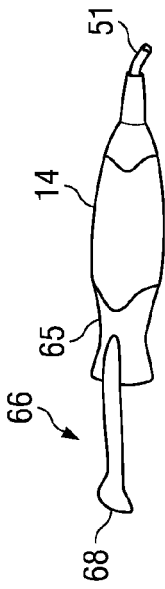
FIG. 4 is a perspective view of a hand-held scanner used to acquire information of an object under scrutiny, suitable for use in the orthodontic care system of FIG. 1.

FIG. 4 is a perspective view of a hand-held scanner 14 used to acquire information of an object under scrutiny, suitable for use in the orthodontic care system of FIG. 1. In one embodiment the elements of the scanner 14 of FIG. 2, including the mirror 54, are contained in the housing 65. The housing 65 is sized and shaped to be held in a human hand. The scanner 14 includes an elongate distal portion 66 having a tip 68. The tip 68 is sized and shaped such that it can be inserted into and moved within an oral cavity of a human so as to enable scanning of anatomical structures inside the oral cavity. The mirror 54 is placed on the underside of the tip 68 to direct the laser beam from the optics of the scanner onto the object and to receive the reflected light beam from the object. The mirror housing has an optional A/C conductive heating coil that heats the mirror 54. The mirror 54 is optionally heated to approximately 40 degrees to prevent fogging of the mirror while the scanner is used in-vivo. One skilled in the art would realize that, besides the A/C conductive heating coil, other methods for heating the mirror 54 can also be used. In another embodiment the elements of the scanner 14' of FIG. 3 are contained in the housing 65.

Figure 5:
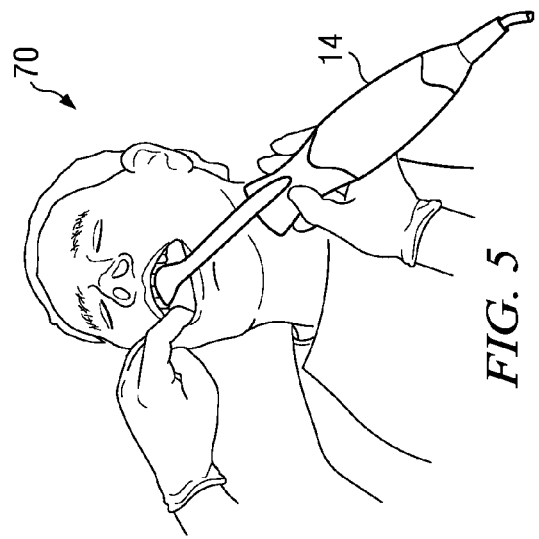
FIG. 5 is an illustration of a patient being scanned with the hand-held scanner of FIG. 4.

FIG. 5 is an illustration of a patient 70 being scanned with the hand-held scanner 14 of FIG. 4. The cheeks and lips are retracted from the teeth and the tip 68 of the scanner is moved over all the surfaces of the teeth in a sweeping motion at a velocity of perhaps 1-2 centimeters per second. The entire upper or lower jaw may need to be scanned in a series of scans, one for the left side, one for the right side, and one for the front. These individual scans are registered to each other as described below. Voice commands or activation of the foot switch (not shown) indicates when each scanning segment is initiated and terminated. The entire process takes just a few minutes.

While FIG. 5 illustrates in-vivo scanning of a human patient, the scanner can of course be used to scan a plaster model of the dentition if that is preferred, or an impression taken from the patient. It is also possible that a scan of a patient may be partially taken in vivo and the remainder from a model or an impression.

Figure 6:
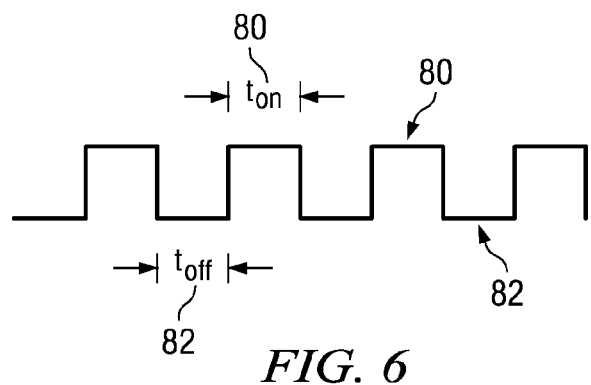
FIG. 6 is an illustration of the pulse sequence and width diagram depicting the operation of the laser 30 of the scanners illustrated in FIGS. 2 and 3 of the preferred embodiments of the invention.

FIG. 6 is an illustration of the pulse sequence and width diagram, pulse width 80 ($t_{on}$) and 82 ($t_{off}$), depicting the operation of the laser 30 of FIGS. 2 and 3. The laser 30 is operated preferably at 10 GHz or higher modulation speed. The pulse width 80 ($t_{on}$) and 82 ($t_{off}$) each at 10 GHz modulation speed is 50 pico seconds (ps). The laser 30 of FIGS. 2 and 3 is operated preferably at wavelength of 1550 nm or 1310 nm. One skilled in the art would appreciate that the laser 30 can be successfully operated at other modulation speeds and wavelengths as well. For in-vivo scanning, medically safe wavelengths are used.

Figure 7:
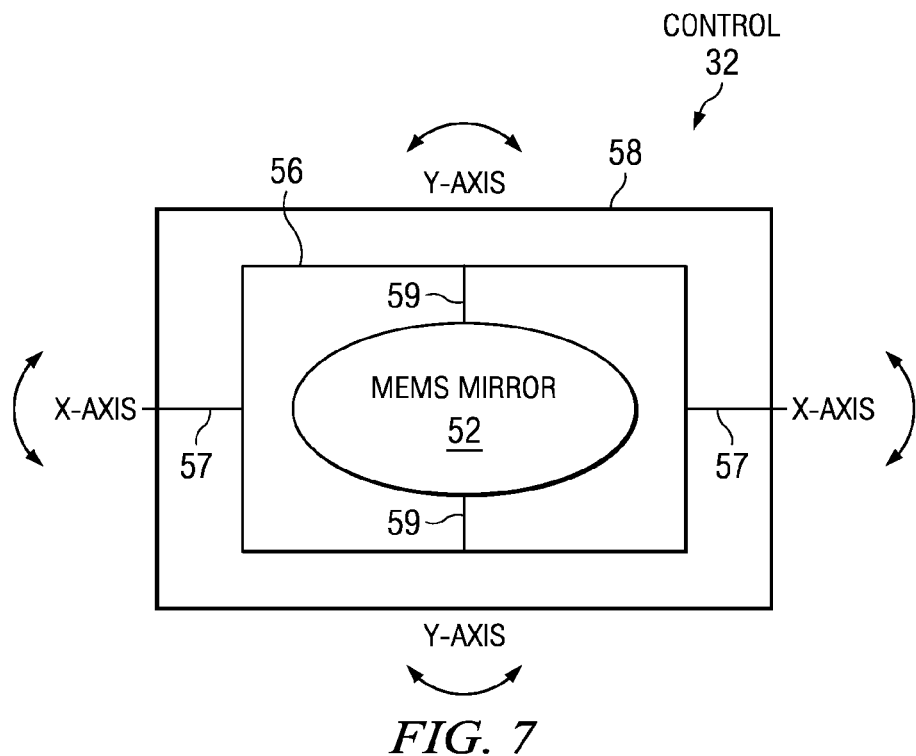
FIG. 7 illustrates a configuration of the MEMS mirror assembly. The MEMS mirror assembly comprises the MEMS mirror 52 of the scanners illustrated in FIGS. 2 and 3 of the preferred embodiments of the invention, and housings.

FIG. 7 illustrates a configuration of the MEMS mirror assembly. Commercially available MEMS mirror is used in the scanning system disclosed herein. The MEMS mirror assembly comprises the MEMS mirror 52 of FIGS. 2 and 3, and housings 56 and 58. The MEMS mirror 52 is mounted on the housing 56 using the hinges 59 which enable the MEMS mirror 52 to oscillate around the y-axis. The housing 56 in turn is mounted on the housing 58 using the hinges 57 which enable the housing 56, and consequently the MEMS mirror 52, to oscillate around the x-axis. The technology uses a resonantly driven MEMS mirror 52 designed for periodical deflection of light through analog voltage control 32. The actuator chip is fabricated with a CMOS compatible micro-machining technology. In a preferred embodiment, the MEMS mirror 52 uses an elliptic silicon plate as mirror plate suspended by two torsion springs as the hinges 57 and two torsion springs as the hinges 59. One skilled in the art would appreciate that other shapes of the MEMS mirror and hinge mechanisms are possible. A gimbal mounting of the mirror plate, very similar to the standard mechanical mirror used in prior generation laser range finding system, is used herein. In a preferred embodiment, the reflectivity of the MEMS mirror plate 52 is designed with a thin layer of aluminum coating achieving the reflection coefficient of approximately 90% at 1550 nm. The glass superstrate that protects the mirror is coated with an antireflection agent. For oscillation during scanning the MEMS plate is excited electrostatically by external square wave voltage applied on the two sides of the hinges 57 and 59 using control 32 which is the same control 32 depicted in FIGS. 2 and 3. The design and fabrication process of the actuator and the electrostatic driving principle enable scan range (optical deflection peak to peak) of up to 60° at 20 V or 35 V. The mirror oscillation frequencies are preferably set at 1.3 kHz on the x-axis and 9.1 kHz on the y-axis; which translates into a frequency-ratio of 1:7 between the oscillation frequency on the x-axis and the oscillation frequency on the y-axis; however other frequencies and frequency-ratios are possible. The design range of the oscillation frequencies are from 150 Hz up to 32 kHz for each of the x and y axes. In a preferred embodiment, the mirror dimensions are 1.5×1.0 mm². One skilled in the art would appreciate that the smaller the mirror size the higher the intrinsic frequency limits. The amplitude of the mechanical oscillation, and therefore the optical deflection angle, is varied by means of the driving voltage at nearly the maximum resonance range limit of the MEMS mirror 52. At large angles the deflection angle depends linearly on the driving voltage. For excitation, a rectangular shaped wave is applied with twice the frequency of the oscillation. The preferred operational voltage for oscillating the MEMS mirror 52 is in the range of 15-35 V peak-to-peak (pp). This level of voltage yields high level of deflection angle repeatability for the MEMS mirror 52. The repeatability is measured as the frequency difference between the driving signal and the detected signal. The repeatability tolerance of 1/1000-1/10000 giving an angular repeatability of $10^{-2}$-$10^{-3}$ degree is realized. Such a low level of tolerance ensures spatial resolution of 20 microns, enabling successful laser ranging with the scanning system 12 of FIG. 2, or the scanning system 12' of FIG. 3.

Figure 8A:
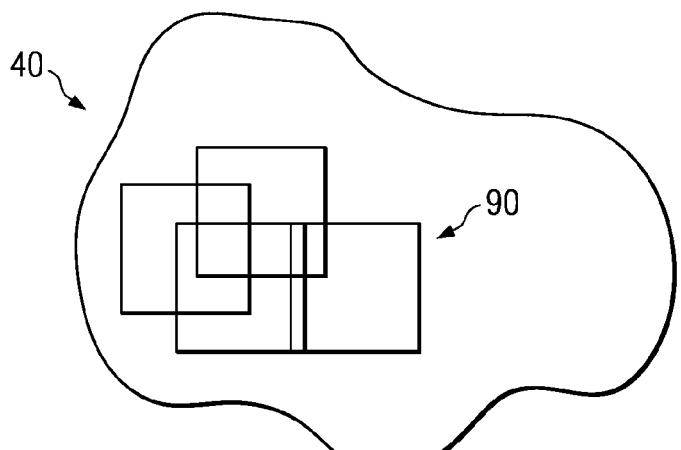
FIGS. 8A-8D illustrate the basic concepts of scanning an object in the form of frames using the scanning system 12 of FIG. 2 or the scanning system 12' of FIG. 3.
Figure 8B:
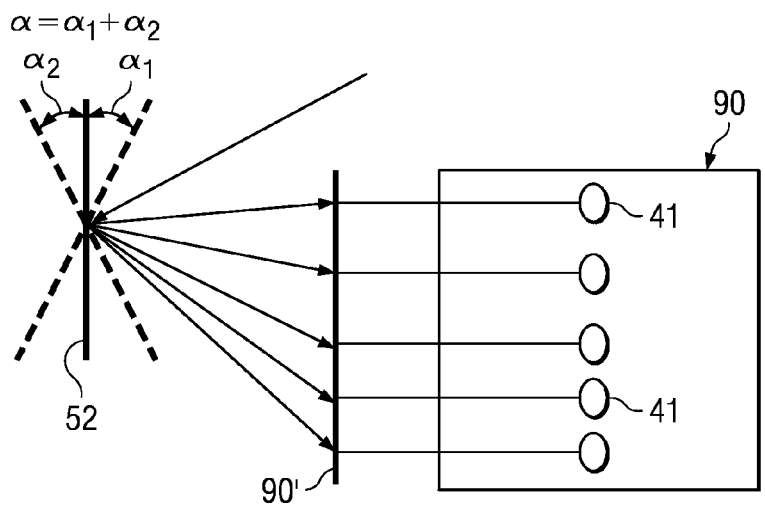
Figure 8C:
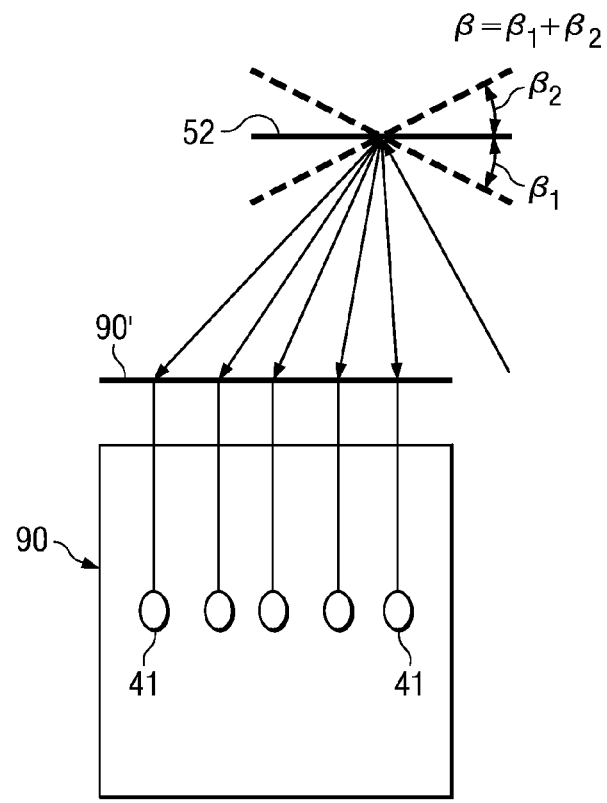
Figure 8D:
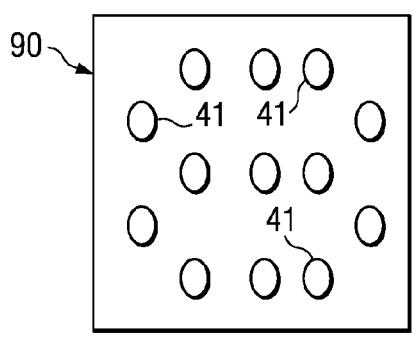

FIGS. 8A-8D illustrate the basic concepts of scanning an object in the form of frames using the scanning system 12 of FIG. 2 or the scanning system 12' of FIG. 3. FIG. 8A illustrates an object 40 with the example scanning frames 90. As shown in FIG. 8A, the surface of the object 40 is scanned in terms of arbitrarily formed frames 90. Preferably a frame overlaps with one or more other frames. A frame 90 in this sense is an area of the surface of an object that can be scanned while keeping the scanner in a stationary position. As noted earlier, the MEMS mirror 52 in FIG. 2 or FIG. 3 is oscillated around the x-axis and simultaneously around the y-axis during the scanning process. Therefore, the size of the frame 90 is determined by the range of oscillations of the MEMS mirror 52 along the x-axis and the y-axis and the distance of the object 40 being scanned from the MEMS mirror 52. For ease of illustration and explanation, the scanner configuration 12' of FIG. 3 is used herein while describing FIGS. 8C-8D; however, the concepts are equally applicable to the scanner configuration 12 of FIG. 2. FIG. 8B illustrates the oscillation of the MEMS mirror 52 along the x-axis by an angle $\alpha_1$ in one direction and an angle $\alpha_2$ in the opposite direction for a total angle $\alpha=\alpha_1+\alpha_2$, while the MEMS mirror 52 is kept in a fixed position along the y-axis. Generally, the rotation is set such that $\alpha_1=\alpha_2$. In this illustration, a side-view of the MEMS mirror 52 when viewed in the direction of the x-axis is shown. As the MEMS mirror 52 is oscillated, the laser beam impacts the surface of the object at points 41 in the frame 90 and is reflected back. Thus, a series of points 41 are scanned. Similarly, FIG. 8C illustrates the oscillation of the MEMS mirror 52 along the y-axis by an angle $\beta_1$ in one direction and an angle $\beta_2$ in the opposite direction for a total angle $\beta=\beta_1+\beta_2$, while the MEMS mirror 52 is kept in a fixed position along the x-axis. Generally again, the rotation is set such that $\beta_1=\beta_2$. In this illustration, a side-view of the MEMS mirror 52 when viewed in the direction of the y-axis is shown. Here again, as the MEMS mirror 52 is oscillated, the laser beam impacts the surface of the object at points 41 in the frame 90 and is reflected back. Thus, a series of points 41 are scanned. In FIGS. 8B and 8C, the frame 90 represents the front view of the object being scanned while the frame 90' represents the side view of the object being scanned. FIG. 8D illustrates the pattern of points 41, and resulting frame 90, that would be realized when the MEMS mirror (not shown for the ease of illustration) is simultaneously oscillated along the x-axis by a total angle α and along the y-axis by a total angle β. A frame comprises the group of points scanned during one complete oscillation cycle of the MEMS mirror along the slow moving axis. In the illustrations described herein, the x-axis oscillates at a slower speed than the y-axis. Therefore, the frame comprises the group of points or pixels scanned during one oscillation cycle of the x-axis. For example, without the loss of generality, a frame would comprise the group of points scanned during the time elapsed between two successive events when the x-axis is at the 0 degree angle position. The points 41 are also referred to herein and elsewhere in this document as pixels. Shown for illustration purposes, the frequency ratio between the oscillation along the x-axis and along the y-axis for the frame 90 in FIG. 8D is 1:2; however, the preferred ratio is 1:7. The type of pixel-pattern illustrated in FIG. 8D is known as the Lissajous pattern in the prior art. One skilled in the art would appreciate that the frequency ratio can be optimized to realize the desired spatial resolution of the surface of the scanned object.

Figure 9A:
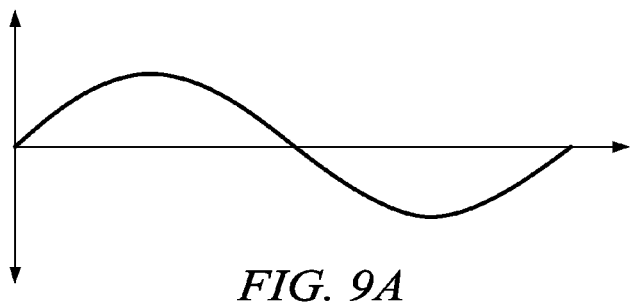
FIGS. 9A-9C illustrate the oscillation cycles for the MEMS mirror.
Figure 9B:
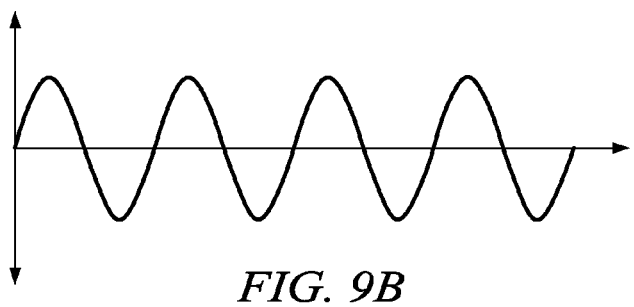
Figure 9C:
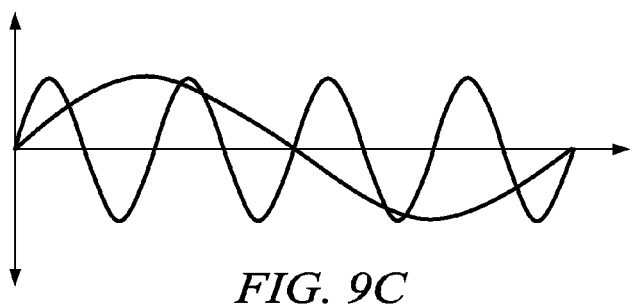

FIGS. 9A-9C illustrate the oscillation cycles for the MEMS mirror. FIG. 9A illustrates four oscillation cycles around the x-axis, FIG. 9B illustrates one oscillation cycle around the y-axis; and FIG. 9C illustrates superimposition of the x-axis oscillation cycles of FIG. 9A and the y-axis oscillation cycle of FIG. 9B.

Once a pixel or a point has been sampled, its range or distance is determined using a prior art range-finding technique. There are several techniques available in the prior art for the ranging measurement and detection including time-of-flight (TOF), amplitude modulation (AM), frequency modulation (FM) and delay oscillator. Any of these techniques can be equally applied with the instant invention. These techniques are discussed in detail elsewhere in literature, so only a brief summary is presented below.

Referring to FIG. 2 or 3, the TOF technique works by pulsing the laser source 22 and gating a counter that measures the transit time from the laser 22 to the target or object 40 and the reflection back from the target or the object 40 at the receiver 24. In a preferred embodiment, the receiver uses an APD to detect the target reflection pulse at much smaller amplitude than the launching pulse. A power threshold determines the signal and clock start and stop gating times. The distance z of the point (or pixel) 41 of the object 40 from the transceiver 15 is determined by the clock time and the speed of light in the traveling space.

$$z = c(t_{stop} - t_{start})/2$$

Where,
c=speed of laser beam or light;
$t_{start}$=the time the laser beam left the laser source 22; and
$t_{stop}$=the time the laser beam reflection detected at the receiver 24.

Again referring to FIG. 2 or 3, the AM laser range-finding works by modulating the amplitude (intensity) of a laser beam 34 and detecting the phase shift in the return beam 62 by synchronous detection at the receiver 24. The range z is indirectly determined by detecting the change in phase between transmitted and received signals.

$$z = c\Delta\Phi/(2\omega)$$

Where,
c=speed of laser beam or light;
$\Delta\Phi$=the phase delay; and
ω=the angular frequency.

Again referring to FIG. 2 or 3, in FM laser range-finding, the frequency of the laser 22 is modulated internally to the laser or externally by a modulator. The frequency is linearly chirped as a function of time creating a sub-carrier multiplexed signal. Coherent detection is used by mixing the reflected signal with a local oscillator source signal and the beat frequency (frequency difference) is measured to derive the range from the following equation.

$$z = c\Delta f/(2A)$$

Where,
c=speed of laser beam or light;
$\Delta f$=the beat frequency; and
A=the frequency linear chirp coefficient.

Again referring to FIG. 2 or 3, in the delay oscillator range finding, the laser 22, the target or the object 40 and the receiver 24 form a closed loop electronic oscillator. The laser beam 36 is turned on and then turned off when the receiver detects the return beam 62. The laser beam 36 is turned back on when the return is no longer detected. This is essentially a ring oscillator with the range is given by the following equation.

$$z = cT$$

Where,
c=speed of laser beam or light; and
T=time period of the oscillation.

The advantage of this technology is that it is simple and cheap for medium range (10 m) applications. The disadvantages are that it is slow and has limited accuracy as a result of single beam mechanical pointing and limited dynamic range.

Figure 10:
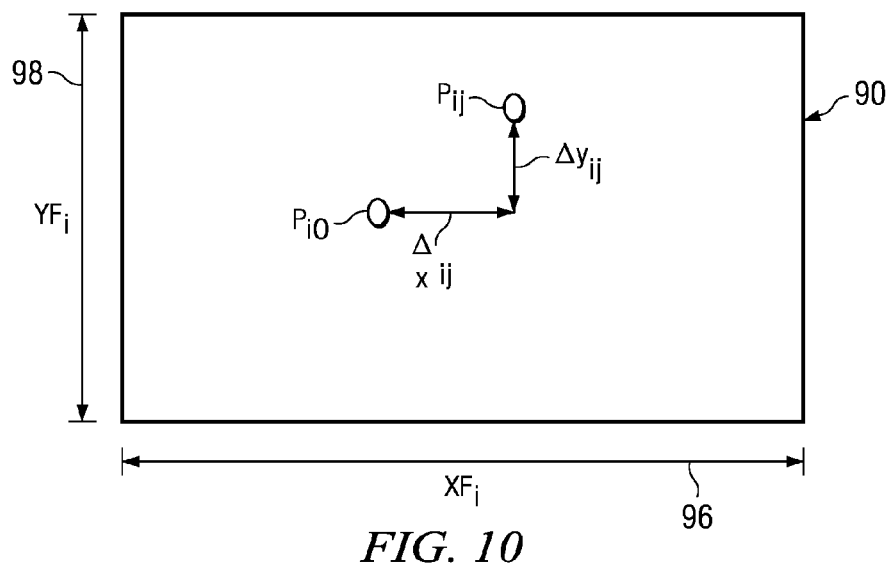
FIG. 10 provides a reference for explaining the method of determining the coordinates for the points scanned from the surface of the object and the frame size.

FIG. 10 provides a reference for explaining the method of determining the coordinates for the points scanned from the surface of the object and the frame size. To begin with, the first point scanned in any frame is designated the reference point for that frame. For example, this point may be the point scanned when the rotational angle is zero degree for both the x-axis and the y-axis for the MEMS 52 in FIG. 2 or FIG. 3. One skilled in the art would appreciate that other points may serve as the reference points for any frame. In FIG. 10 scanned point $P_{i0}$ is designated the reference point for a frame, say frame i. Then the distance $L_{i0}$ for the point $P_{i0}$ from the scanner is determined by:

$$L_{i0} = c(t_{stopi0} - t_{starti0})/2 \qquad \text{Eq. (1);}$$

where,
c=speed of laser beam or light;
$t_{starti0}$=the time the laser beam left the laser source 22 in FIG. 2 or FIG. 3 for scanning the point $P_{i0}$; and
$t_{stopi0}$=the time the laser beam reflection detected at the receiver 24 in FIG. 2 or FIG. 3 for scanning the point $P_{i0}$.

Then, the dimensions for the frame 90 in FIG. 10, frame i, $XF_i$ in the x direction 96 and $YF_i$ in the y direction 98 are given by:

$$XF_i = 2 L_{i0}(\tan \alpha) \qquad \text{Eq. (2);}$$

and $$YF_i = 2 L_{i0}(\tan \beta) \qquad \text{Eq. (3);}$$

where,
$L_{i0}$ is given by Eq. (1);
α=the maximum angle of rotation along the x-axis of the MEMS mirror 52 in FIG. 2 and FIG. 3; and
β=the maximum angle of rotation along the y-axis of the MEMS mirror 52 in FIG. 2 and FIG. 3.

The reference point $P_{i0}$ is assigned arbitrary x and y coordinates $x_{i0}$ and $y_{i0}$, which may be set equal to zero; and the z coordinate is $z_{i0}=L_{i0}$.

The differences for the coordinates in the x and y directions for point $P_{ij}$ and the point $P_{i0}$ in frame 90 are given by:

$$\Delta x_{ij}=L_{i0}(\tan \alpha_{ij}) \quad \text{Eq. (4);}$$

and $$\Delta y_{ij}=L_{i0}(\tan \beta_{ij}) \quad \text{Eq. (5);}$$

where, $L_{i0}$ is given by Eq. (1);

$\alpha_{ij}$=the angle of rotation along the x-axis of the MEMS mirror 52 in FIG. 2 and FIG. 3 while scanning point $P_{ij}$; and $\beta_{ij}$=the angle of rotation along the y-axis of the MEMS mirror 52 in FIG. 2 and FIG. 3 while scanning point $P_{ij}$.

It should be noted that either or both of $\Delta x_{ij}$ and $\Delta y_{ij}$ could be positive or negative depending upon the angles $\alpha_{ij}$ and $\beta_{ij}$.

Now the x and y coordinates for the point $P_{ij}$, $x_{ij}$ and $y_{ij}$, are given by:

$$x_{ij}=x_{i0}+\Delta x_{ij} \quad \text{Eq. (6);}$$

and $$y_{ij}=y_{i0}+\Delta y_{ij} \quad \text{Eq. (7).}$$

The z coordinate for the point $P_{ij}$, $z_{ij}$, is given by:

$$z_{ij}=c(t_{stopij}-t_{startij})/2 \quad \text{Eq. (8);}$$

where, c=speed of laser beam or light;

$t_{startij}$=the time the laser beam left the laser source 22 in FIG. 2 or FIG. 3 for scanning the point $P_{ij}$; and $t_{stopij}$=the time the laser beam reflection detected at the receiver 24 in FIG. 2 or FIG. 3 for scanning the point $P_{ij}$.

As noted earlier, the mirror oscillation frequencies are preferably set at 1.3 kHz on the x-axis and 9.1 kHz on the y-axis; which translates into a frequency-ratio of approximately 1:7 between the oscillation frequency on the x-axis and the oscillation frequency on the y-axis; however other frequencies and frequency-ratios are possible. At the oscillation frequency of 1.3 kHz on the x-axis, 1300 frames per second are scanned.

In another embodiment of the invention, a large number of scanning samples, e.g., 100-1,000, are taken and the dimensions averaged over the number of samples to get much better accuracy, by a factor at least equivalent to the square-root of the number of samples averaged, in determining the x, y, and z coordinates for each point scanned from the surface of an object. At 10 GHz laser modulation speed, the complete pulse time, which is equivalent to the time elapsed between consecutive samples, is 100 ps. Therefore, at this laser speed, the time needed to obtain 100 samples, excluding the pulse travel time, is 1 ns, and the time for 1,000 samples is 10 ns. However, during the time period while the samples are being gathered, the scanner does not remain focused on the same single point because of the oscillations in the MEMS mirror; and that introduces an error in the distance measurement. However, the error is very insignificant compared to the improvement in the accuracy of the distance measurement. The area of the object surface covered by the laser beam during the sample gathering time period is a function of the MEMS mirror oscillation speed along the x and y axes and the distance of the object surface being scanned from the scanner. At the MEMS preferred oscillation speed of 1.3 kHz along the x-axis, and 9.1 kHz along the y-axis; and assuming that the frame size on the surface of the object being scanned is approximately 10 mm×10 mm, which is often the typical case in in-vivo scanning the dentition of a patient, the object surface area corresponding to 100 samples or 1 ns is approximately 0.026 μm×0.18 μm, and the object area corresponding to 1,000 samples or 10 ns is approximately 0.26 μm×1.8 μm. It is therefore evident that the error introduced by the MEMS mirror oscillations during the sample gathering period is insignificant and that the instant invention provides highly accurate data of the scanned surface of an object. This is particularly true when the object being scanned has a significantly larger surface area than the distance measurement error mentioned above, and the surface is relatively smooth.

To migrate from conventional laser ranging to high-speed ranging, the table below summarizes the major development in the path for high-speed and high resolution ranging. Fundamentals to achieving the improved performance are major advances in low-cost, high-speed optoelectronics and faster scanning mirrors. As a result, it becomes possible to achieve better resolution at smaller time intervals or near-real time to capture 3D digital information using the laser and MEMS based scanner described in this specification.

|  | Prior Art | Instant Invention | Units | Improvement Factor |
| --- | --- | --- | --- | --- |
| Laser pulse width | 10 | 0.1 | ns | 100 |
| Receiver time resolution | 5 | 0.01 | ns | 500 |
| Averaging cycles | 150 | 30 | times | 5 |
| Scan speed | 50 | 10,000 | Hz | 200 |
| Accuracy | 2.5 | 0.025 | mm | 100 |

Figure 11:
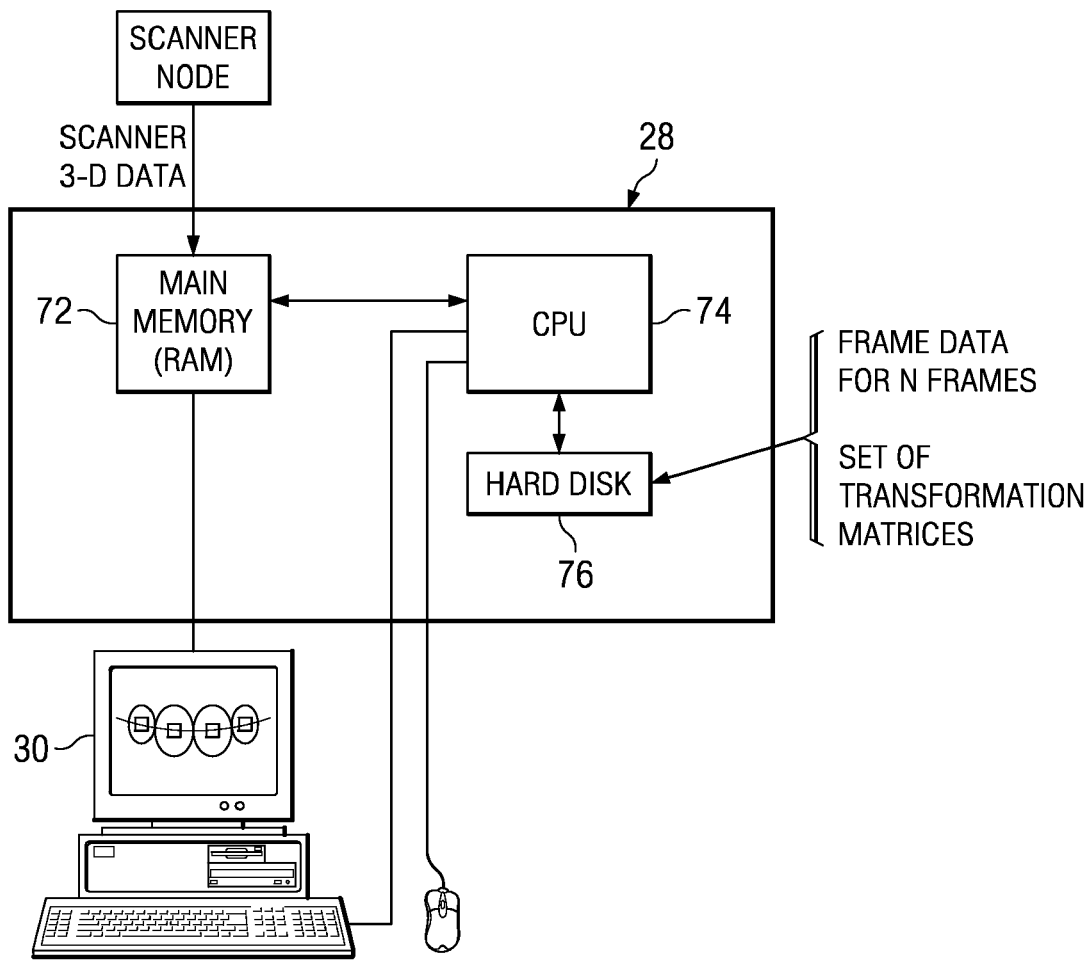
FIG. 11 is a block diagram of the back office server of FIG. 1 showing the elements used to calculate the digital model of the patient's dentition and display the digital model on a screen display of the server.

FIG. 11 is a block diagram of the back office server of FIG. 1 showing the elements used to calculate the digital model of the patient's dentition. After the scanning workstation has processed all the images captured by the scanner and generated a set of three-dimensional frames, the frame data is transmitted to the back office server 28. The back office server 28 performs a registration process for the frames and generates and displays the digital model on a screen display 30. The registration can be done on a real-time basis while the object is being scanned; and the scanned model displayed to the user. The raw scanner data in the form of three-dimensional frames is stored in the main computer memory 72. The frame data for N captured frames, i=1 . . . N from the scanner is stored in the hard disk 74. The hard disk also stores a set of (N−1) transformation matrices $[T]_i$, for i=2−N. The transformation matrices basically contain information as to how each frame of three-dimensional points needs to be translated and rotated in a three-axis Cartesian coordinate system in order to be registered with the other frames in a best-fit manner. One of the frames, such as the first frame in the series, is a starting point for registration and no transformation matrix is obtained for that frame. The generation of the transformation matrices, and use of the matrices with the frame data to generate the three dimensional model, is described in further detail below.

There is no need to know the separation distance between the scanner and the object being scanned, or any absolute value of the location of the object in any global coordinate system. The scanner allows for truly reference independent scanning, yet it gives very precise description of the three-dimensional surface.

Since the scanner and scanned object move relative to each other during capture of the scanned frames, the three dimensional coordinates for a large number of frames will not agree with each other. In other words, the X, Y and Z coordinates for a given point on the object will change from frame to frame since the point was scanned from a different spatial orientation for each image. Hence, the frames have to be registered to each other to generate a complete overall digital model of the object. Various registration procedures to be performed on the frames, to find a best-fit solution for coordinates of the object in one frame vis-à-vis coordinates of the object in other frames are briefly described in the following section, and in detail in the U.S. patent application of Rudger Rubbert et al., filed Apr. 13, 2001, Ser. No. 09/834,593, entitled "SCANNING SYSTEM AND CALIBRATION METHOD FOR CAPTURING PRECISE THREE-DIMENSIONAL INFORMATION OF OBJECTS," pending, the entire contents of which are fully incorporated by reference herein.

Figure 12:
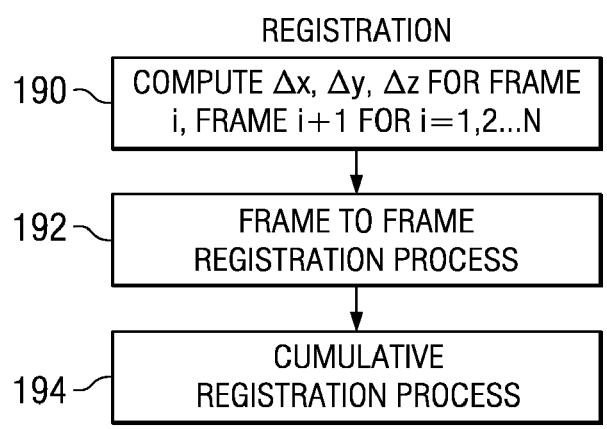
FIG. 12 is a flow chart illustrating the steps performed to generate a complete three-dimensional model using the registration process.

FIG. 12 is a flow chart illustrating the steps performed to generate a complete three-dimensional model of the dentition of a patient from a series of scans of the upper and lower jaws. The steps include an initial step 190 of determining an entry point into a registration process, a frame to frame registration process 192 of registering one frame to another, and finally a cumulative registration procedure 194 in which the frames are registered to all other frames to obtain a slightly more accurate model of the object than that obtained by frame to frame registration. It will be understood that depending on the application a frame to frame registration may only be needed, or the user may only desire a cumulative registration and step 192 is not performed at all.

Figure 13A:
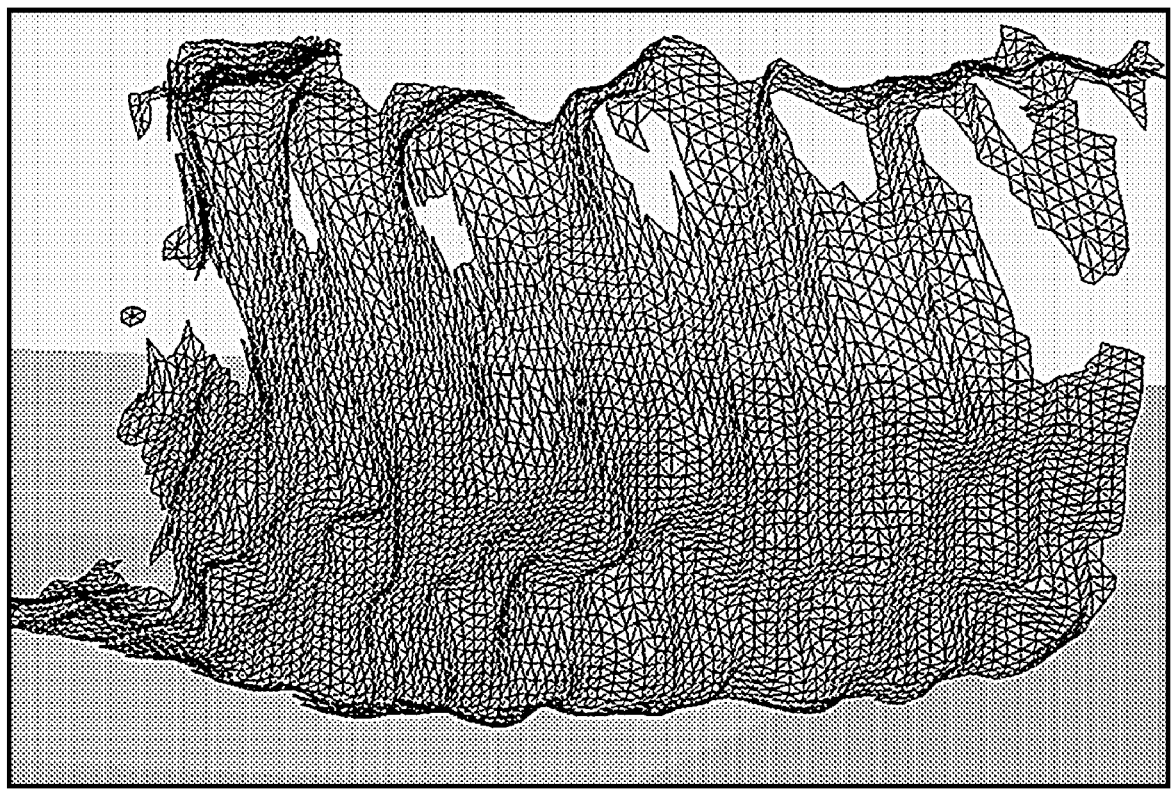
FIG. 13A is a view of the three-dimensional surface obtained by scanning an object according to the invention disclosed herein. The scanned points have been connected into triangles during the registration process.
Figure 13B:
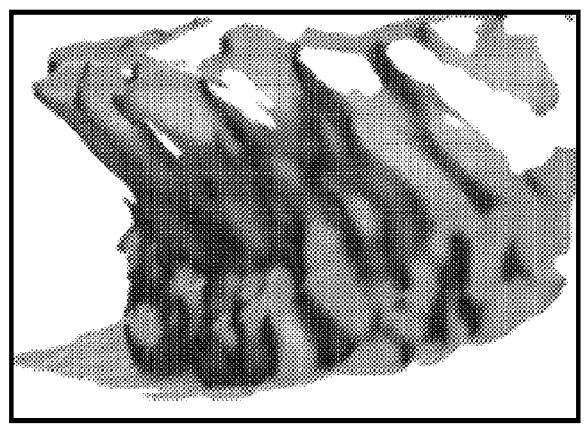
FIG. 13B is a view of the object in FIG. 13A in the finished form.

The result of registration is a three-dimensional model containing all the points from the frames captured by the scanner. An example of such a model is shown in FIGS. 13A and 13B.

Registration processes require a starting point for fitting one frame, frame i to another frame, frame i+1. The starting point, in the illustrated embodiment, is rough calculation of the offset between overlapping points in the frames in X, Y and Z directions. Whereas prior art systems have good pre-knowledge of the spatial relationship due to the known physical arrangement of the scanner and the object, the present system does not. The starting point is the initial assumption of spatial relationship between one frame and the previous frame (and one frame and a set of previous frames).

Frame to frame registration is a process for registering one frame with another frame, that is, finding a best-fit in terms of translation and rotation make overlapping points in the frames agree with each other. If the frames are generated in sequential order, frame to frame registration refers to registration of the second frame to the first frame, the third frame to the second frame, from the fourth frame to the third frame, etc. Frame to frame registration can be performed very quickly. It can be performed in a manner such that the operator of the scanning system sees the results of frame to frame registration on the monitor of the scanning workstation while they are still scanning the patient. What they see is an accurate three-dimensional representation of the dentition on the monitor, for those portions of the dentition that have been scanned thus far. As additional frames are obtained, they are registered to the previous frame and added to the computer model. When scanning is complete, the computer model can be rotated around on the monitor and inspected to see that all relevant portions of the teeth and anatomical structures have been scanned. The user thus gets immediate feedback on the results of the scanning using frame to frame registration.

Each frame is typically generated from a different spatial orientation of the scanner relative to the object due to movement of the scanner during frame capture, hence the frames overlap to at least some extent. The registration process is used to find a best fit between the frames relative to each other, and thereby provide a complete three-dimensional virtual model of the surface of the object from all of the frames. The end result of the frame to frame registration is a substantially exact three dimensional model of the scanned object. This object is represented by a large set of point coordinates in computer memory. The result is also represented as a set of transformation matrices providing information as to how each frame of points should be translated and rotated in three dimensions in order to fit to the previous frame.

The frame to frame registration process is also an iterative process. At the end of each iteration, a comparison is made as to how "close" the two frames are to each other in three dimensions. If they are not close enough (with "closeness" determined in absolute terms by a quality index, say in microns), another iteration is done, using the results of the first iteration. The frame to frame process may continue for tens or even hundreds of iterations, depending on how fine or precise the user wants the registration to be. The process stops when a best fit between two frames has been reached or a maximum number of iterations have occurred.

Cumulative registration is an alternative or improvement to a frame to frame registration. The difference between the two is that frame to frame registration only registers one frame to one other frame, whereas cumulative registration is a registration of a frame to more than one other frame, such as where one frame is registered to all previously registered frames. An advantage of cumulative registration is more accuracy in the resulting three-dimensional model. The disadvantage is that cumulative registration can be significantly more computationally intensive.

FIG. 13A is a view of the three-dimensional surface obtained by scanning an object according to the invention disclosed herein. The scanned points have been connected into triangles during the registration process. FIG. 13A is an enlarged view of the scanned object. FIG. 13B is a view of the object in FIG. 13A in the finished form.

It is contemplated that the inventive scanning system and method of scanning can be used on virtually any type of object. The medical field is only one example of where three-dimensional information of a surface may be a valuable piece of information, and can be easily and quickly attained with the scanning system of the present invention. These other possible uses of the scanner for other types of objects are considered within the scope of the invention.

Precise three dimensional information of an object may be useful in the world of art as a way of authenticating a painting or sculpture. The work, or perhaps some portion of the work, is scanned. A registration is performed of the scanned images to create a complete three-dimensional model of the work. The model is archived or stored in memory, for example in a computer of a museum or gallery owning the work. Any work purporting to be that work of art that should later appear on the art market (e.g., if the work is lost or stolen), can be verified by scanning the work or the portion of the work. Then, a comparison of the three-dimensional model of the original work to the three-dimensional model of the work purporting to be the work can be made. Any substantial deviation from the original to the purported work will reveal the purported original to be a forgery. Thus, in another aspect of the invention, a machine-readable memory is provided that is accessible by a computing device. The memory comprises data storage regions storing surface information in three dimensions of at least a portion of a work of art. The surface information is obtained by scanning the work of art with a scanner and calculating the surface information in three dimensions from a series of images obtained by the scanner.

Furthermore, a memory may be created storing three-dimensional models of a large number of works, for example the works in the Museum of Modern Art in New York City. This archive can be used for authentication of any work of art that may be stolen or lost from the museum and later recovered.

The capability of the scanning system to store or archive accurate three dimensional models of objects can be a powerful tool in a variety of fields, including archeology, paleontology, forensic science, historic preservation and architecture, and other industrial or medical areas. As noted above, the scanner optics will be designed to have the proper range of focus and angle between projection and imaging axes to record images of these types of objects. The principles of operation of the scanner are applicable to all of these potential uses of the invention.

In another embodiment of the invention, a method of scanning the three-dimensional surface of an object is disclosed, comprising the steps of:

(a) positioning a scanner proximate to an object, the scanner having an oscillating MEMS mirror for directing a laser beam emitting from a light source towards an object and a means for capturing the reflected laser beam off of the surface of the object;

(b) scanning, with the scanner, while keeping the scanner in substantially stationary position relative to the object, a frame from the surface wherein the frame comprises a group of points on the surface scanned during a complete oscillation cycle of the MEMS mirror, wherein the scanning step comprises scanning every point in the frame and wherein the step of scanning a point comprises the sub-steps of:

(i) emitting a laser beam from the light source towards the oscillating MEMS mirror;

(ii) directing the emitted laser beam using the oscillating MEMS mirror towards the surface whereby the surface reflects the emitted laser beam upon impact on the surface;

(iii) receiving the laser beam reflected by the surface into a receiver using the means for capturing the reflected laser beam;

(iv) recording, with a processing unit, the timing parameters of the emitted laser beam and the reflected laser beam and the oscillation angles of the oscillating MEMS mirror;

(v) computing from the timing parameters and the oscillation angles, using the processing unit, a three-dimensional mapping information of the point on the surface; and (vi) storing the computed three-dimensional mapping information of the point of the surface in a memory;

(c) moving the scanner and the object relative to each other; and (d) repeating steps (b) and (c) and capturing, with the scanner, a series of frames off of the surface of the object as the scanner and the surface move relative to each other;

(e) processing the series of frames, each of the frames comprising spatial coordinates for the group of points in the frame, and (f) registering overlapping areas of the frames to each other to generate a three-dimensional virtual model of the object.

The scanner can be used to scan in-vivo the teeth of a patient, or scan a physical model of the teeth of the patient to derive a virtual model of the dentition of the patient.

Although the preferred embodiment of the scanner disclosed herein comprises a two-dimensional MEMS mirror, one skilled in the art would appreciate that other scanner configurations, such as for example comprising two one-dimensional MEMS mirrors that oscillate only along a single axis, are possible.

While a presently preferred embodiment of the invention has been described with particularity, variation from the illustrated embodiment is possible without departure from the scope of the invention. This scope is to be determined by reference to the appended claims.

We claim:

1. A scanner system for mapping the three-dimensional surface of an object, comprising:
 a laser light source;
 an oscillating Micro-Electro-Mechanical Systems ("MEMS") mirror;
 a receiver;
 a processing unit; and
 a memory;
 wherein said laser light source emits a beam towards said MEMS mirror;
 wherein said MEMS mirror, while oscillating, reflects said beam;
 wherein said beam reflected by said MEMS mirror impacts a group of one or more points on said surface of said object dependent upon position of said MEMS mirror during an oscillation cycle;
 wherein each of said group of one or more points on said surface of said object further reflects said beam;
 wherein said receiver receives said beam further reflected by each of said group of one or more points on said surface of said object;
 wherein said processing unit comprises computer instructions enabling monitoring of parameters comprising (a) characteristics of (i) said beam emitted by said laser light source and (ii) said beam further reflected by each of said group of one or more points on said surface of said object and received by said receiver; (b) (i) emission beginning timing of said beam emitted by said laser light source and (ii) receipt timing of said beam further reflected by each of said group of one or more points on said surface of said object and received by said receiver; and (c) oscillation angles of said oscillating MEMS mirror; and computer instructions for computing from said parameters a three-dimensional mapping information of said surface of said object;
 wherein said laser light source and said MEMS mirror are movable for scanning different areas of said surface of said object;
 wherein said memory stores said three-dimensional mapping information of said surface of said object.

2. The scanner system of claim 1, wherein said laser light source emits said beam modulated at a frequency of 10 GHz or higher.

3. The scanner system of claim 1, wherein said laser light source emits said beam at a wavelength of 1550 nm or 1310 nm.

4. The scanner system of claim 1, wherein said oscillating MEMS mirror is mounted on a pair of housings enabling oscillation of said MEMS mirror on an x-axis at speed x and a y-axis at speed y; wherein said y-axis is perpendicular to said x-axis.

5. The scanner system of claim 4, wherein the ratio of said speed x to said speed y is 1:7.

6. The scanner system of claim 4, wherein said speed x is 1.3 kHz and said speed y is 9.1 kHz.

7. The scanner system of claim 1, wherein said oscillating MEMS mirror is circular in shape.

8. The scanner system of claim 1, wherein said oscillating MEMS mirror is elliptical in shape.

9. The scanner system of claim 1, wherein said emitted beam from said laser light source is collimated prior to reaching said oscillating MEMS mirror.

10. The scanner system of claim 9, wherein said oscillating MEMS mirror reflects said emitted beam into a beam splitter wherein said beam splitter directs said emitted laser beam towards a static mirror wherein said static mirror reflects said emitted beam on to said surface of said object.

11. The scanner system of claim 10, wherein said collimator, said MEMS mirror and said beam splitter are contained in a housing sized and shaped to be held in a human hand.

12. The scanner system of claim 11, wherein said housing further comprises a distal portion holding said static mirror, and wherein said distal portion is sized and shaped so as to be insertable into and moveable within an oral cavity of a human for scanning of anatomical structures inside the oral cavity.

13. The scanner system of claim 12, wherein said static mirror is heated while scanning said object.

14. The scanner system of claim 1, wherein said beam reflected by said surface of said object passes through a beam splitter prior to reaching said receiver.

15. The scanner system of claim 1, wherein said receiver has a sensitivity of 10 pico-seconds rise time.

16. The scanner system of claim 1, wherein a frame comprises said group of one or more points on said surface of said object; and wherein said processing unit further comprises computer instructions for executing a registration algorithm for creating a virtual model of said object from said frames of said surface of said object.

17. The scanner system of claim 16, wherein said memory and said processing unit are located in a scanning workstation, said scanning workstation further comprising a monitor operatively connected to said processing unit, said monitor displaying three-dimensional images of said object during or after scanning of said surface of said object.

18. The scanner system of claim 16, wherein said computer instructions perform a frame-to-frame registration.

19. The scanner system of claim 16, wherein said computer instructions perform a cumulative registration.

20. The scanner system of claim 1, wherein said object comprises one or more teeth.

21. The scanner system of claim 1, wherein said object comprises a work of art.

22. The scanner system of claim 1, wherein said object comprises a human body.

23. The scanner system of claim 1, wherein said object comprises a work piece.

24. A method of scanning the three-dimensional surface of an object, comprising the steps of:
   (a) positioning a scanner proximate to an object; said scanner having a light source and an oscillating Micro-Electro-Mechanical Systems ("MEMS") mirror; said MEMS mirror directing a laser beam emitting from said light source towards a surface of an object; said scanner further having a means for capturing said laser beam reflected off of said surface of said object;
   (b) scanning, with said scanner, while keeping said scanner in substantially stationary position relative to said object, a frame from said surface wherein said frame comprises a group of points on said surface scanned during a complete oscillation cycle of said MEMS mirror, wherein said scanning step comprises scanning every point in said frame and wherein the step of scanning a point comprises the sub-steps of:
      (i) emitting said laser beam from said light source towards said oscillating MEMS mirror;
      (ii) directing said emitted laser beam using said oscillating MEMS mirror towards said point on said surface whereby said point on said surface reflects said emitted laser beam upon impact on said point on said surface;
      (iii) receiving the laser beam reflected by said point on said surface into a receiver using said means for capturing the reflected laser beam;
      (iv) recording, with a processing unit, parameters comprising (a) characteristics of (i) said laser beam emitted by said light source and (ii) said laser beam reflected by said point on said surface of said object and received by said receiver; (b) (i) emission beginning timing of said laser beam emitted by said light source and (ii) receipt timing of said laser beam reflected by said point on said surface and received by said receiver; and (c) oscillation angle of said oscillating MEMS mirror;
      (v) computing from said parameters, using said processing unit, a three-dimensional mapping information of said point on said surface; and
      (vi) storing said computed three-dimensional mapping information of said point of said surface in a memory;
   (c) moving said scanner and said object relative to each other; and
   (d) repeating steps (b) and (c) and capturing, with said scanner, a series of frames off of said surface of said object as said scanner and said surface move relative to each other;
   (e) processing said series of frames, each of said frames comprising spatial coordinates for said group of points in said frame, and
   (f) registering overlapping areas of said frames to each other to generate a three-dimensional virtual model of said object.

25. The method of claim 24, wherein step (f) is performed using frame-to-frame registration.

26. The method of claim 25, further comprising the step of executing a cumulative registration algorithm to register said series of frames to derive said three-dimensional model of said surface of said object.

27. The method of claim 24, wherein step (e) of processing comprises the sub-steps of:
   (a) calculating z coordinate of said point using a range finding technique; and
   (b) calculating x and y coordinates of said point.

28. The method of claim 24, wherein said scanner comprises a hand-held unit.

29. The method of claim 24, wherein said scanner is used to obtain a three-dimensional model of an anatomical structure.

30. The method of claim 29, wherein said anatomical structure comprises teeth.

31. The method of claim 30, wherein said teeth are scanned in-vivo with said scanner.

32. The method of claim 31, wherein said scanner comprises a housing having a distal portion holding a static mirror, and wherein said distal portion is sized and shaped so as to be insertable into and moveable within an oral cavity of a human for scanning of anatomical structures inside the oral cavity.

33. The method of claim 32, wherein said static mirror is heated while scanning said oral cavity of said human.

34. The method of claim 30, wherein a physical model is made from said anatomical structure and wherein said scanner scans said physical model.

35. The method of claim 34, wherein said physical model comprises a model of a patient's teeth and surrounding anatomical structures.

36. A scanner system for mapping the three-dimensional surface of an object, comprising:
   a laser light source;
   a collimator;
   an oscillating Micro-Electro-Mechanical Systems ("MEMS") mirror;
   a receiver;
   a beam splitter;
   a static mirror;
   a processing unit; and
   a memory;
   wherein said laser light source emits a beam towards said collimator;
   wherein said collimator collimates said beam emitted from said laser light source and transmits said collimated beam towards said MEMS mirror;
   wherein said MEMS mirror, while oscillating, reflects said collimated beam towards said beam splitter;
   wherein said beam splitter directs said beam reflected by said MEMS mirror towards said static mirror;
   wherein said static mirror further reflects said beam on to surface of an object;
   wherein said surface of said object reflects said beam;
   wherein said receiver receives said beam reflected by said surface of said object;
   wherein said processing unit comprises computer instructions enabling monitoring of parameters comprising (a) characteristics of (i) said beam emitted by said laser light source and (ii) said beam further reflected by said surface of said object and received by said receiver; (b) (i) emission beginning timing of said beam emitted by said laser light source and (ii) receipt timing of said beam reflected by said surface of said object and received by said receiver; and (c) position of said oscillating MEMS mirror; and computer instructions for computing there from a three-dimensional mapping information of said surface of said object;
   wherein said memory stores said three-dimensional mapping information of said surface of said object.

37. The scanner system of claim 36, wherein said laser light source emits said beam modulated at a frequency of 10 GHz or higher.

38. The scanner system of claim 36, wherein said laser light source emits said beam at a wavelength of 1550 nm or 1310 nm.

39. The scanner system of claim 36, wherein said MEMS mirror is mounted on a pair of housings enabling oscillation of said MEMS mirror on an x-axis at speed x and a y-axis at speed y; wherein said y-axis is perpendicular to said x-axis.

40. The scanner system of claim 39, wherein the ratio of said speed x to said speed y is 1:7.

41. The scanner system of claim 39, wherein said speed x is 1.3 kHz and said speed y is 9.1 kHz.

42. The scanner system of claim 39, wherein said beam reflected by said MEMS mirror impacts a group of one or more points on said surface of said object depending upon position of said MEMS mirror during an oscillation cycle; wherein said group of one or more points on said surface of said object constitutes a frame.

43. The scanner system of claim 42, wherein said laser light source and said MEMS mirror are movable for scanning different areas of said surface of said object thereby producing multiple frames.

44. The scanner system of claim 43, wherein said processing unit further comprises computer instructions enabling frame-to-frame registration of said frames thereby mapping said surface of said object in three-dimension.

45. The scanner system of claim 43, wherein said processing unit further comprises computer instructions enabling cumulative registration of said frames thereby mapping said surface of said object in three-dimension.

46. The scanner system of claim 36, wherein said MEMS mirror is circular in shape.

47. The scanner system of claim 36, wherein said MEMS mirror is elliptical in shape.

48. The scanner system of claim 36, wherein said beam reflected by said surface of said object passes through second beam splitter prior to reaching said receiver.

49. The scanner system of claim 36, wherein said receiver has a sensitivity of 10 pico-seconds rise time.

50. The scanner system of claim 36, wherein said collimator, said MEMS mirror and said beam splitter are contained in a housing sized and shaped to be held in a human hand.

51. The scanner system of claim 50, wherein said housing further comprises a distal portion holding said static mirror, and wherein said distal portion is sized and shaped so as to be insertable into and moveable within an oral cavity of a human for scanning of anatomical structures inside the oral cavity.

52. The scanner system of claim 36, wherein said memory and said processing unit are located in a scanning workstation, said scanning workstation further comprising a monitor operatively connected to said processing unit, said monitor displaying three-dimensional images of said object during or after scanning of said surface of said object.

53. The scanner system of claim 36, wherein said object comprises one or more teeth.

54. The scanner system of claim 36, wherein said object comprises a work of art.

55. The scanner system of claim 36, wherein said object comprises a human body.

56. The scanner system of claim 36, wherein said object comprises a work piece.

* * * * *